(12) United States Patent
Li et al.

(10) Patent No.: US 8,334,297 B2
(45) Date of Patent: Dec. 18, 2012

(54) 2,4-PYRIMIDINEDIAMINE COMPOUNDS FOR TREATMENT OF INFLAMMATORY DISORDERS

(75) Inventors: Hui Li, Santa Clara, CA (US); Esteban Masuda, Menlo Park, CA (US); Stephanie Yung, San Francisco, CA (US); Taisei Kinoshita, San Mateo, CA (US); Rongxian Ding, San Francisco, CA (US); Rajinder Singh, Belmont, CA (US); Tarikere Gururaja, Santa Clara, CA (US); Donald G. Payan, Hillsborough, CA (US); Kin Tso, San Francisco, CA (US)

(73) Assignee: Rigel Pharmaceuticals Inc., South San Francisco, CA (US)

( * ) Notice: Subject to any disclaimer, the term of this patent is extended or adjusted under 35 U.S.C. 154(b) by 275 days.

(21) Appl. No.: 12/687,053

(22) Filed: Jan. 13, 2010

(65) Prior Publication Data

US 2010/0179164 A1    Jul. 15, 2010

Related U.S. Application Data

(60) Provisional application No. 61/144,616, filed on Jan. 14, 2009.

(51) Int. Cl.
*A01N 43/54* (2006.01)
*A61K 31/505* (2006.01)
(52) U.S. Cl. ...................... 514/275; 544/324
(58) Field of Classification Search .................. 544/323, 544/324
See application file for complete search history.

(56) References Cited

U.S. PATENT DOCUMENTS

| | | | |
|---|---|---|---|
| 7,998,969 B2 * | 8/2011 | Kestesz et al. | 514/272 |
| 2007/0203161 A1 | 8/2007 | Argade et al. | |
| 2007/0293494 A1 * | 12/2007 | Djung et al. | 514/235.5 |

FOREIGN PATENT DOCUMENTS

WO   WO 2008071587 A2 *   6/2008

OTHER PUBLICATIONS

European Search Report for European Application No. 10732053.3, dated Jun. 13, 2012, 6 pages.

* cited by examiner

*Primary Examiner* — James O Wilson
*Assistant Examiner* — Alexander R Pagano
(74) *Attorney, Agent, or Firm* — Rudy J. Ng; Carol L. Francis; Bozicevic, Field & Francis LLP

(57) ABSTRACT

2,4-Pyrimidinediamine compounds represented by formula (I), methods for preparing the same and methods for treating an inflammatory disorder and for inhibiting the production of IL-23 and/or stimulating the production of IL-10 using the same:

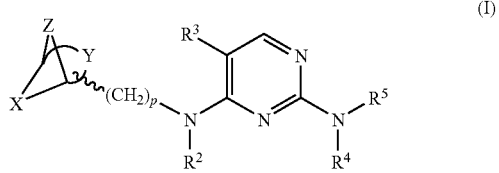

26 Claims, No Drawings

2,4-PYRIMIDINEDIAMINE COMPOUNDS FOR TREATMENT OF INFLAMMATORY DISORDERS

CROSS REFERENCE TO RELATED APPLICATION

This application claims priority benefit under 35 U.S.C. §119(e) to U.S. Provisional Patent Application No. 61/144,616, filed on Jan. 14, 2009, which is incorporated by reference in its entirety.

INTRODUCTION

Interleukin 23 (IL-23) is a heterodimeric cytokine consisting of two subunits, p40 and p19. IL-23 plays a role in the inflammatory response against infection, and has been implicated in the development of multiple sclerosis, inflammatory bowel disease, and cancer. Interleukin 10 (IL-10) is an anti-inflammatory cytokine that is capable of inhibiting the syntheses of various pro-inflammatory cytokines.

Inflammation is the complex biological response of vascular tissues to harmful stimuli, such as pathogens, damaged cells, or irritants. However, inflammation which runs unchecked can lead to a host of disorders, such as inflammatory arthritis, rheumatoid arthritis, hay fever, and atherosclerosis.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Acute inflammation is a short-term process which is characterized by the classic signs of inflammation—swelling, redness, pain, heat, and loss of function—due to the infiltration of the tissues by plasma and leukocytes. It occurs as long as the injurious stimulus is present and ceases once the stimulus has been removed, broken down, or walled off by scarring (fibrosis).

Prolonged inflammation, known as chronic inflammation, leads to a progressive shift in the type of cells which are present at the site of inflammation and is characterized by simultaneous destruction and healing of the tissue from the inflammatory process. Chronic inflammation is a pathological condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. Endogenous causes include persistent acute inflammation. Exogenous causes are varied and include bacterial infection, prolonged exposure to chemical agents such as silica, or autoimmune reactions such as rheumatoid arthritis.

Cells of the immune system use a signal cascade to mount an escalating response to a real or perceived insult. The inflammatory response becomes pathogenic when the signal cascade is invoked inappropriately. For example, autoimmune diseases are the consequence of the immune system mounting a response against antigens which are intrinsic. Many anti-inflammatory agents function by inhibiting the signal cascade, such as by blocking intracellular or intercellular effectors. Glucocorticoids, for example, mimic the natural immune suppressant, cortisol, to block genes at the transcription level, and cyclo-oxygenase inhibitors are small molecules that bind to and inhibit an enzyme that processes an internal signal molecule in cells.

SUMMARY

Described herein are 2,4-pyrimidinediamine compounds. Also described are methods for preparing the compounds, and the methods for treating inflammatory disorders. Further described are methods for inhibiting IL-23 production.

DETAILED DESCRIPTION

As used herein, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Described herein are 2,4-pyrimidinediamine compounds represented by the following formula (I):

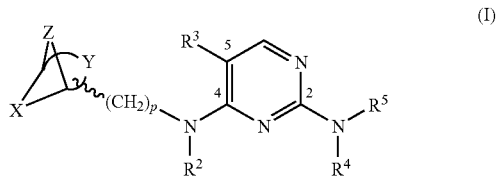

In the formula (I), X represents $(CH_2)_m$ wherein m is an integer from 1 to 4, and wherein one or more $CH_2$ is optionally replaced with O, S or $N(R^{01})$, wherein $R^{01}$ represents H, $C_1$-$C_7$ alkyl or $C_3$-$C_8$ cycloalkyl. In an embodiment, m is 2. In a further embodiment, X represents $(CH_2)_2$. The term "alkyl," as used herein, denotes both straight- and branched-chain alkyls. Specific examples of $C_1$-$C_7$ alkyls include, but are not limited to, methyl, ethyl, propyl, butyl, pentyl, hexyl and heptyl and their branched-chain isomers, e.g., isopropyl, isobutyl, sec-butyl, tert-butyl, etc. The term "cycloalkyl," as used herein, denotes both monocyclic and bicyclic alkyls. Specific examples of $C_3$-$C_8$ cycloalkyl include, but are not limited to, cyclopropyl, cyclobutyl, cyclopentyl, cyclohexyl, cycloheptyl and cyclooctyl, their substituted isomers, e.g., methyl cyclopentyl, methyl cyclohexyl, and their bicyclic isomers, e.g., spiro[3,4]octyl and spiro[3,3]heptyl, and the like.

Y represents $(CH_2)_n$ wherein n is an integer from 2 to 5, and wherein one or more $CH_2$ is optionally replaced with O, S or $N(R^{02})$, wherein $R^{02}$ represents H, $C_1$-$C_7$ alkyl or $C_3$-$C_8$ cycloalkyl. In an embodiment, n is 3. In a further embodiment, Y represents $(CH_2)_3$.

Z represents a heteroatom, such as $N(R^1)$, O and S, wherein $R^1$ represents H, $C_1$-$C_7$ alkyl or $C_3$-$C_8$ cycloalkyl.

In an embodiment, $R^1$ represents $C_1$-$C_7$ alkyl, such as $CH_3$. In a further embodiment, Z represents $N(C_1$-$C_7$ alkyl$)$, such as $N(CH_3)$.

Specific examples of suitable bicyclic structures represented by

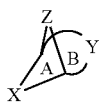

include, but are not limited to the following:

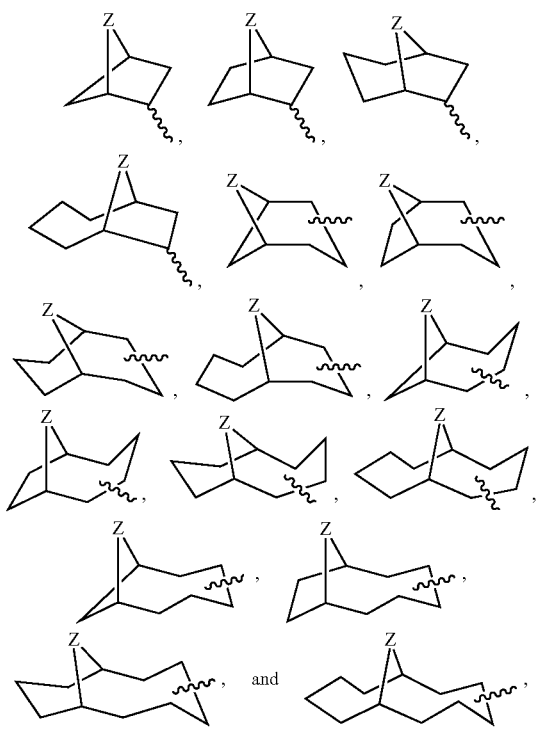

wherein any ring atoms and bridgehead atoms are optionally replaced with O, S or $N(R^0)$ wherein $R^0$ represents H, $C_1$-$C_7$ alkyl or $C_3$-$C_8$ cycloalkyl, and wherein ⁓ may be attached to any ring atom in ring B, except the atom represented by Z. In an embodiment, ⁓ is attached to a carbon ring atom.

One of skill in the art will appreciate that many of the compounds, as well as the various compound species specifically described and/or illustrated herein, may exhibit tautomerism, conformational isomerism, geometric isomerism and/or optical isomerism. The term "tautomer" refers to alternate forms of a molecule that differ only in electronic bonding of atoms and/or the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible. For example, the disclosed compounds may include a stereogenic element, such as one or more chiral centers and/or double bonds, and as a consequence, may exist as stereoisomers, such as cis-trans isomers, E and Z isomers, enantiomers and diastereomers and mixtures thereof, including racemic and optically active mixtures. The term "stereoisomer" refers to isomeric molecules whose atomic connectivity is the same but whose atomic arrangement in space is different. The term "enantiomers" refers to compound that are stereoisomers that are nonsuperimposable complete minor images of each other. The term "diastereomers" refers to a pair of stereoisomers that are not mirror images of each other and one or more stereogenic centers differ between the two stereoisomers, or one or more chiral centers have opposite configurations between the two stereoisomers. The term "racemic" refers to a mixture of equal moles of an optically active isomer and its enantiomer.

In certain embodiments, the disclosed 2,4-pyrimidinediamine compounds are in the form of pharmaceutically acceptable salts. Generally, pharmaceutically acceptable salts are those that retain substantially one or more of the desired pharmacological activities of the parent compound and which are suitable for administration to a subject. Examples of the presently disclosed compounds include at least one basic amino group. Thus, pharmaceutically acceptable salts of such compounds include acid addition salts formed with inorganic acids or organic acids. Inorganic acids suitable for forming pharmaceutically acceptable acid addition salts with the present compounds include, by way of example, hydrohalide acids (hydrochloric acid, hydrobromic acid, hydroiodic acid), sulfuric acid, nitric acid, phosphoric acid, and the like. Organic acids suitable for forming pharmaceutically acceptable acid addition salts include, without limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (such as, methanesulfonic acid, ethanesulfonic acid, 1,2-ethane-disulfonic acid, 2-hydroxyethanesulfonic acid), arylsulfonic acids (such as benzenesulfonic acid, 4chlorobenzenesulfonic acid, 2-naphthalenesulfonic acid, 4-toluenesulfonic acid, camphorsulfonic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In the formula (I), ⁓ when attached to a stereogenic element, such as a chiral center or double bond, indicates that the bond can be attached in either configuration. With continued reference to formula (I), when attached to the bicyclic structure

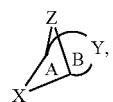

⁓ represents a bond of either possible relative or absolute stereochemistry. Compounds described herein having such bicyclic systems may have substituents attached in an endo configuration, an exo configuration, or both. The stereochemical descriptor "endo" refers to a bridge substituent that points toward the larger of the remaining two bridges. If the substituent points toward the smaller remaining bridge, it is referred to as an "exo" substituent. In compounds having a chiral center, the symbol ～～ is used to indicate that the chiral center may have the configuration, R or S, or both.

In certain embodiments, the above bicyclic structure has the formula:

The structure

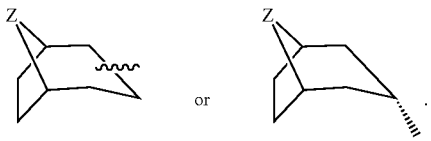

has the endo configuration. As noted above, the compounds disclosed herein may exist in several tautomeric forms. For example, ketone compounds may exist in the enol form, the keto form and mixtures thereof. As the various compound names, formulae and compound drawings within the specification and claims may represent only one of the possible tautomeric, conformational isomeric, optical isomeric or geometric isomeric forms, it should be understood that tautomeric, conformational isomeric, optical isomeric and/or geometric isomeric forms of the disclosed compounds, as well as mixtures of these various different isomeric forms, also are intended.

In the formula (I), p is 0 or 1.

In the formula (I), $R^2$ represents H, $C_1$-$C_7$ alkyl or $C_2$-$C_8$ alkanoyl. $R^4$ represents H, $C_1$-$C_7$ alkyl or $C_2$-$C_8$ alkanoyl. In an embodiment, $R^2$ and $R^4$ are H.

In the formula (I), $R^3$ represents H, halogen, cyano, nitro, ($C_1$-$C_7$ alkoxy)carbonyl, $C_1$-$C_7$ alkyl, $C_1$-$C_7$ haloalkyl, $C_1$-$C_7$ alkoxy or $C_1$-$C_7$ haloalkoxy. The term "alkoxy," as used herein, denotes groups having straight- or branched-chain alkyls. Specific examples of $C_1$-$C_7$ alkoxy include methoxy, ethoxy, propoxy, butoxy, pentyloxy, hexyloxy and heptyloxy and their branched-chain isomers, e.g., isopropoxy, isobutoxy, sec-butyloxy, tert-butyloxy, etc. The term "halo-," as used herein, denotes halogens including fluoro-, chloro-, bromo- and iodo-, and, for example, fluoro- and chloro-. The haloalkyl and haloalkoxy may have one or more halogen substituent(s) at any suitable position(s) on the alkyl chain.

Specific examples of suitable haloalkyl include, but are not limited to, chloromethyl, dichloromethyl, trichloromethyl, bromomethyl, fluoromethyl, difluoromethyl, trifluoromethyl, 1-fluoroethyl, 1-chloroethyl, 2-chloroethyl, 2,2,2-trichloroethyl, 2,2,2-trifluoroethyl, 1,2-dichloroethyl, 1-chloropropyl, 3-chloropropyl, 1-chlorobutyl, 1-chloropentyl, 1-chlorohexyl, 4-chlorohexyl, 4-chlorobutyl and the like.

Specific examples of suitable haloalkoxy include, but are not limited to, chloromethoxy, dichloromethoxy, trichloromethoxy, bromomethoxy, fluoromethoxy, difluoromethoxy, trifluoromethoxy, 1-fluoroethoxy, 1-chloroethoxy, 2-chloroethoxy, 2,2,2-trichloroethoxy, 2,2,2-trifluoroethoxy, 1,2-dichloroethoxy, 1-chloropropoxy, 3-chloropropoxy, 1-chlorobutoxy, 1-chloropentyloxy, 1-chlorohexyloxy, 4-chlorohexyloxy, 4-chlorobutoxy and the like.

In an embodiment, $C_1$-$C_7$ haloalkyl is $CHF_2$ or $CF_3$. In a further embodiment, $R^3$ represents F, $CF_3$, CN, $NO_2$, or $COOCH_2CH_3$. In another embodiment, $R^3$ represents F.

In the formula (I), $R^5$ represents substituted aryl or heteroaryl. The term "substituted" or "substituent," as used herein, denotes an atom or group of bonded atoms replaced a hydrogen atom in a parent molecule. In an embodiment, aryl or heteroaryl encompassed by $R^5$ has 6 to 14 ring atoms. The term "aryl," as used herein, denotes monocyclic and polycyclic aromatic systems. In an embodiment, the aryl encompassed by $R^5$ represents substituted phenyl or naphthyl. The term "heteroaryl," as used herein, denotes monocyclic and polycyclic aromatic systems having one or more, and, for example, up to 5, heteroatoms selected from the group consisting of O, S and N. In an embodiment, the heteroaryl contains one or two O, S or $N(R^{03})$ wherein $R^{03}$ represents H, $C_1$-$C_7$ alkyl or $C_3$-$C_8$ cycloalkyl. Specific examples of suitable heteroaryls include, but are not limited to, thienyl, furyl, furazanyl, pyrrolyl, imidazolyl, pyrazolyl, isothiazolyl, isoxazolyl, pyridyl, pyrazinyl, pyrimidinyl, pyridazinyl, benzofuranyl, isobenzofuranyl, indolizinyl, indolyl, isoindolyl, 1H-indazolyl, purinyl, quinolyl, isoquinolyl, phthalazinyl, naphthyridinyl, quinoxalinyl, quinazolinyl, cinnolinyl, pteridinyl, and the like.

When $R^5$ represents substituted heteroaryl, the heteroaryl may be connected to the N2 atom through any atom in the ring therein, and, for example, through a carbon atom.

In an embodiment, the substituted aryl or heteroaryl encompassed by $R^5$ are disubstituted. In a further embodiment, the disubstitution occurs at the positions which are meta- and para- to the position through which the aryl or heteroaryl is connected to the N atom. In another embodiment, $R^5$ represents substituted aryl or heteroaryl having 6 ring atoms.

In a further embodiment, $R^5$ represents the following formula:

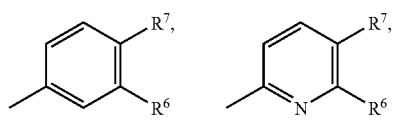

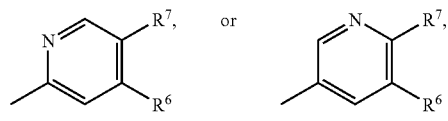

wherein $R^6$ and $R^7$ each independently represents H, halogen, cyano, $C_1$-$C_7$ alkyl, $C_1$-$C_7$ haloalkyl, $C_1$-$C_7$ alkoxy, $C_1$-$C_7$ haloalkoxy, $C_3$-$C_8$ cycloalkyl, —$SO_2$—$C_3$-$C_8$ cycloalkyl, $C_3$-$C_8$ cycloalkyl-$SO_2$—$R^8$, $C_3$-$C_8$ cycloalkyl, —$SO_2$-$C_3$-$C_8$ cycloalkenyl, $C_3$-$C_8$ cycloalkenyl-$SO_2$—$R^8$, aryl, —$SO_2$-aryl, aryl-$SO_2$—$R^8$, a heterocyclic group, a —$SO_2$-heterocyclic group, a heterocyclic-$SO_2$—$R^8$ group, or —$SO_2$—$NR^9R^{10}$; or $R^6$ and $R^7$ are combined to form a ring together with the carbon atoms to which they are bonded. $R^8$ and $R^9$ each independently represents $C_1$-$C_7$ alkyl or $C_3$-$C_8$ cycloalkyl, and $R^{10}$ represents H, $C_1$-$C_7$ alkyl or $C_3$-$C_8$ cycloalkyl.

In a further embodiment, $R^5$ represents the following formula:

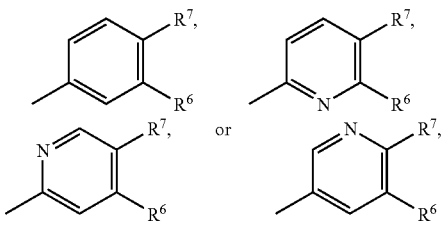

wherein $R^6$ represents halogen, cyano, $C_1$-$C_7$ alkyl, $C_1$-$C_7$ haloalkyl, $C_1$-$C_7$ alkoxy or $C_1$-$C_7$ haloalkoxy; and $R^7$ represents H, $C_1$-$C_7$ alkyl, $C_1$-$C_7$ haloalkyl, $C_1$-$C_7$ alkoxy, $C_1$-$C_7$ haloalkoxy, $C_3$-$C_8$ cycloalkyl, —$SO_2$-$C_3$-$C_8$ cycloalkyl, $C_3$-$C_8$ cycloalkyl-$SO_2$—$R^8$, $C_3$-$C_8$ cycloalkyl, —$SO_2$-$C_3$-$C_8$ cycloalkenyl, $C_3$-$C_8$ cycloalkenyl-$SO_2$—$R^8$, aryl, —$SO_2$-aryl, aryl-$SO_2$—$R^8$, a heterocyclic group, a —$SO_2$-heterocyclic group, a heterocyclic-$SO_2$—$R^8$ group, or —$SO_2$—$NR^9R^{10}$. $R^8$ and $R^9$ each independently represents $C_1$-$C_7$ alkyl or $C_3$-$C_8$ cycloalkyl, and $R^{10}$ represents H, $C_1$-$C_7$ alkyl or $C_3$-$C_8$ cycloalkyl.

In an embodiment, $R^6$ represents Cl, CN, $CF_3$, or $OCHF_2$.

The term "cycloalkenyl," as used hwwwerein, denotes both monocyclic and bicyclic alkenyls. Specific examples of $C_3$-$C_8$ cycloalkenyls include, but are not limited to, cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl and their substituted derivatives, e.g., methyl cyclobutenyl, methyl cyclopentenyl, methyl cyclohexenyl, and the like, and their bicyclic isomers.

The term "heterocyclic group," as used herein, denotes aromatic, aliphatic and unsaturated, mono- and poly-cyclic groups having one or more heteroatoms. The polycyclic group may contain two or more spiro, fused or bridged rings.

In an embodiment, the heterocyclic group has 1 to 3 rings. In another embodiment, the heterocyclic group has 3 to 14 carbon ring atoms, at least one of which is replaced with a heteroatom, such as O, S or $N(R^{03})$ wherein $R^{03}$ represents H, $C_1$-$C_7$ alkyl or $C_3$-$C_8$ cycloalkyl.

The heterocyclic group may be attached through any ring atom therein. In an embodiment, $R^7$ represents a heterocyclic group which is attached through a N ring atom.

Specific examples of suitable heterocyclic groups include, but are not limited to, aziridinyl, oxiranyl, thiiranyl, azetidinyl, oxetanyl, thietanyl, pyrrolidinyl, tetrahydrofuryl, tetrahydrothienyl, piperidyl, tetrahydropyranyl, tetrahydrothiopyranyl, tetrahydropyridyl, tetrahydroquinolyl, tetrahydroisoquinolyl, morpholinyl, thiomorpholinyl, piperazinyl, dioxolanyl, imidazolidinyl, oxazolidinyl, isoxazolidinyl, thiazolidinyl, pyrazolidinyl, 2H-pyrrolyl, pyrrolinyl, imidazolinyl, pyrazolinyl, dihydrofuryl, dihydrothienyl, dihydropyranyl, dihydrothiopyranyl, dihydropyridyl, dihydroquinolyl, dihydroisoquinolyl, indolinyl, isoindolinyl, furyl, furazanyl, pyranyl, thienyl, pyrrolyl, pyrazolyl, imidazolyl, triazolyl, tetrazolyl, oxazolyl, oxadiazolyl, isoxazolyl, thiazolyl, isothiazolyl, pyridyl, pyridazinyl, pyrimidinyl, pyrazinyl, triazinyl, benzopyranyl, benzofuranyl, indolyl, quinolinyl and the like. In these groups, the attachment may occur at a hetero ring atom or a carbon ring atom therein.

In an embodiment, $R^7$ has the following formula:

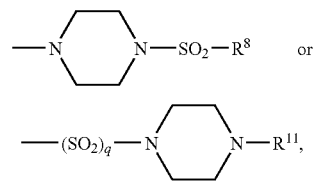

wherein q represents 0 or 1, and $R^{11}$ represents H or $C_1$-$C_7$ alkyl. In a further embodiment, $R^8$ represents methyl.

In another embodiment, $R^7$ represents one of the following formulae:

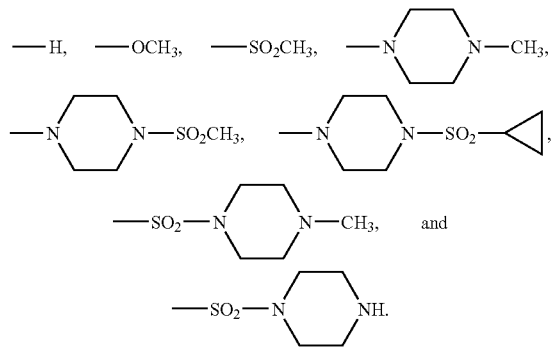

Alternatively, $R^6$ and $R^7$ may be combined to form a heterocyclic ring together with the carbon atoms to which they are bonded. For example, $R^6$ and $R^7$ may be combined to form one of the following rings together with the carbon atoms to which they are bonded:

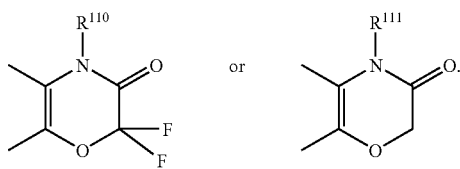

$R^{110}$ is H, $C_1$-$C_7$ alkyl or $C_2$-$C_8$ alkanoyl. $R^{111}$ is H, $C_1$-$C_7$ alkyl or $C_2$-$C_8$ alkanoyl. In certain embodiments, $R^{110}$ is H or $C_1$-$C_7$ alkyl. In certain embodiments, $R^{111}$ is H or $C_1$-$C_7$ alkyl.

Alternatively, $R^6$ and $R^7$ may be combined to form a heterocyclic ring together with the carbon atoms to which they are bonded. For example, $R^6$ and $R^7$ may be combined to form one of the following rings together with the carbon atoms to which they are bonded:

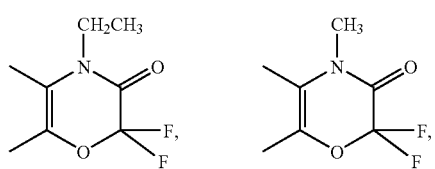

-continued

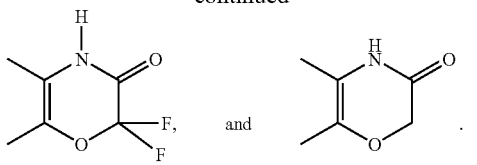

In one embodiment, the 2,4-pyrimidinediamine compound has one of the following formulae (II) to (V):

(II)
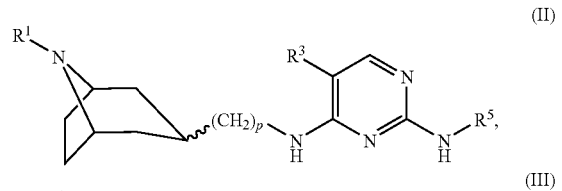

(III)
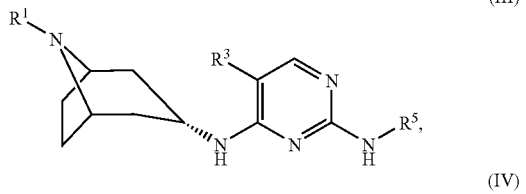

(IV)
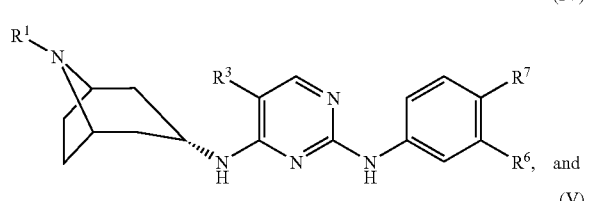

(V)
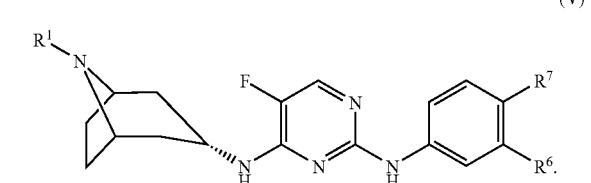

$R^1$, $R^3$, $R^5$, $R^6$, $R^7$ and p in the above formulae (II) to (V) have the same meanings as defined with respect to formula (I). In one embodiment, $R^6$ represents halogen or $C_1$-$C_7$ haloalkyl, and, for example, Cl or $CF_3$.

In one embodiment, the compound has the formula (I) having an endo configuration, wherein X represents $(CH_2)_2$, Y represents $(CH_2)_3$, Z represents $N(R^1)$ wherein $R^1$ represents H, $C_1$-$C_7$ alkyl or $C_3$-$C_8$ cycloalkyl, p is 0 or 1, $R^2$ and $R^4$ are H, $R^3$ represents halogen, cyano, nitro, ($C_1$-$C_7$ alkoxy) carbonyl, or $C_1$-$C_7$ haloalkyl, $R^5$ represents the following formula:

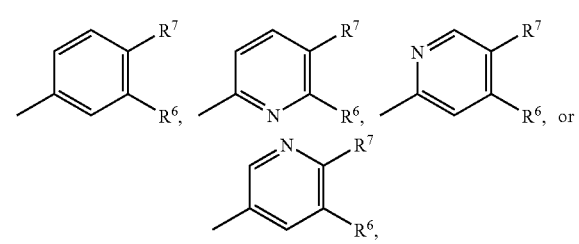

$R^6$ represents halogen, cyano, $C_1$-$C_7$ haloalkyl, or $C_1$-$C_7$ haloalkoxy, and $R^7$ represents H, $C_1$-$C_7$ alkoxy, a heterocyclic group, a —$SO_2$-heterocyclic group, or a heterocyclic-$SO_2$— $R^8$ group, wherein $R^8$ represents $C_1$-$C_7$ alkyl or $C_3$-$C_8$ cycloalkyl. In a further embodiment, $R^3$ represents F. In another further embodiment, $R^6$ represents Cl, CN, $CF_3$, or $OCHF_2$. In another further embodiment, $R^7$ represents:

H, $C_1$-$C_7$ alkoxy,

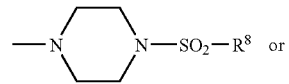

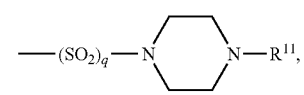

wherein q represents 0 or 1, and $R^{11}$ represents H or $C_1$-$C_7$ alkyl.

In another embodiment, the compound has the formula (I) having an endo configuration, wherein X represents $(CH_2)_2$, Y represents $(CH_2)_3$, Z represents $N(R^1)$ wherein $R^1$ represents H, $C_1$-$C_7$ alkyl or $C_3$-$C_8$ cycloalkyl, p is 0 or 1, $R^2$ and $R^4$ are H, $R^3$ represents halogen, cyano, nitro, ($C_1$-$C_7$ alkoxy) carbonyl, or $C_1$-$C_7$ haloalkyl, $R^5$ represents the following formula:

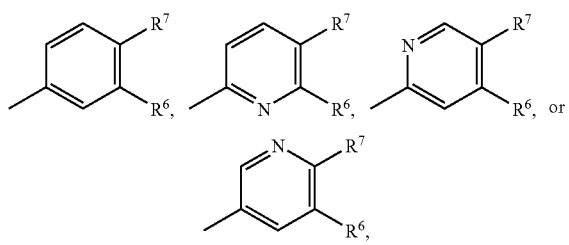

$R^6$ and $R^7$ are combined to form one of the following rings together with the carbon atoms to which they are bonded:

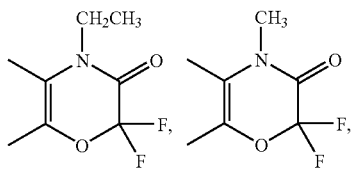

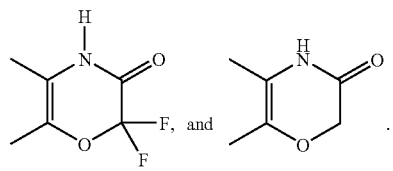

In a further embodiment, $R^3$ represents F.

In another embodiment, the compound has the formula (I) having an endo configuration, wherein X represents $(CH_2)_2$, Y represents $(CH_2)_3$, Z represents $N(R^1)$ wherein $R^1$ represents H, $C_1$-$C_7$ alkyl or $C_3$-$C_8$ cycloalkyl, p is 0, $R^2$ and $R^4$ are H, $R^3$ represents F, $CF_3$, CN, $NO_2$, or $COOCH_2CH_3$, $R^5$ represents the formula

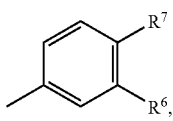

$R^6$ represents Cl, CN, $CF_3$, or $OCHF_2$, and $R^7$ represents: H, $OCH_3$,

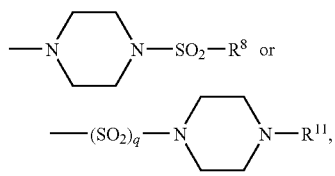

wherein q represents 0 or 1, and $R^{11}$ represents H or $C_1$-$C_7$ alkyl. In a further embodiment, $R^3$ represents F.

In another embodiment, the compound has the formula (I) having an endo configuration, wherein X represents $(CH_2)_2$, Y represents $(CH_2)_3$, Z represents $N(R^1)$ wherein $R^1$ represents H, $C_1$-$C_7$ alkyl or $C_3$-$C_8$ cycloalkyl, p is 0, $R^2$ and $R^4$ are H, $R^3$ represents F, $CF_3$, CN, $NO_2$, or $COOCH_2CH_3$, $R^5$ represents the formula

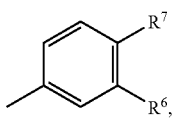

$R^6$ and $R^7$ are combined to form one of the following rings together with the carbon atoms to which they are bonded:

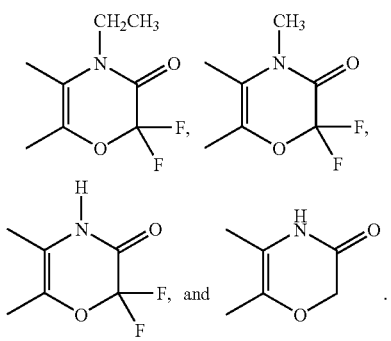

In a further embodiment, $R^3$ represents F. In another further embodiment, $R^6$ and $R^7$ are combined to form, together with the carbon atoms to which they are bonded,

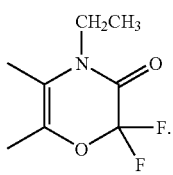

The disclosed compounds are further described in the following non-limiting embodiments.

Embodiment 1: A compound according to the following formula (I):

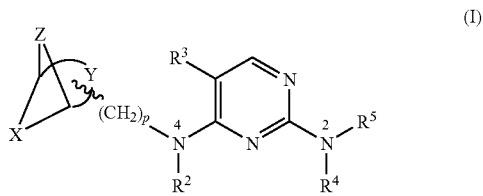

wherein

X represents $(CH_2)_m$ wherein m is an integer from 1 to 4, and wherein one or more $CH_2$ is optionally replaced with O, S or $N(R^{O1})$, wherein $R^{O1}$ represents H, $C_1$-$C_7$ alkyl or $C_3$-$C_8$ cycloalkyl;

Y represents $(CH_2)_n$ wherein n is an integer from 2 to 5, and wherein one or more $CH_2$ is optionally replaced with O, S or $N(R^{O2})$, wherein $R^{O2}$ represents H, $C_1$-$C_7$ alkyl or $C_3$-$C_8$ cycloalkyl;

Z represents $N(R^1)$, O or S, wherein $R^1$ represents H, $C_1$-$C_7$ alkyl or $C_3$-$C_8$ cycloalkyl;

∼∼∼ represents a bond having an endo-configuration, an exo-configuration, or a mixture thereof;

p is 0 or 1;

$R^2$ represents H, $C_1$-$C_7$ alkyl or $C_2$-$C_8$ alkanoyl;

$R^3$ represents H, halogen, cyano, nitro, ($C_1$-$C_7$ alkoxy)carbonyl, $C_1$-$C_7$ alkyl, $C_1$-$C_7$ haloalkyl, $C_1$-$C_7$ alkoxy or $C_1$-$C_7$ haloalkoxy;

$R^4$ represents H, $C_1$-$C_7$ alkyl or $C_2$-$C_8$ alkanoyl; and $R^5$ represents substituted aryl or heteroaryl.

Embodiment 2: A compound according to Embodiment 1, wherein X represents $(CH_2)_2$.

Embodiment 3: A compound according to Embodiment 1 or 2, wherein Y represents $(CH_2)_3$.

Embodiment 4: A compound according to any one of the proceeding Embodiments, wherein Z represents $N(R^1)$ and wherein $R^1$ represents H, $C_1$-$C_7$ alkyl.

Embodiment 5: A compound according to any one of the proceeding Embodiments, wherein ∼∼∼ represents a bond having an endo-configuration.

Embodiment 6: A compound according to any one of the proceeding Embodiments, wherein p is 0 or 1.

Embodiment 7: A compound according to any one of the proceeding Embodiments, wherein p is 0.

Embodiment 8: A compound according to any one of the proceeding Embodiments, wherein $R^2$ and $R^4$ each represents H.

Embodiment 9: A compound according to any one of the proceeding Embodiments, wherein $R^3$ represents H, halogen, cyano, nitro, ($C_1$-$C_7$ alkoxy)carbonyl, $C_1$-$C_7$ alkyl, $C_1$-$C_7$ haloalkyl, $C_1$-$C_7$ alkoxy or $C_1$-$C_7$ haloalkoxy.

Embodiment 10: A compound according to any one of the proceeding Embodiments, wherein $R^3$ represents F, $CF_3$, CN, $NO_2$, or $COOCH_2CH_3$.

Embodiment 11: A compound according to any one of the proceeding Embodiments, wherein $R^3$ represents F.

Embodiment 12: A compound according to any one of the proceeding Embodiments, wherein $R^5$ represents substituted aryl or heteroaryl having 6 ring atoms.

Embodiment 13: A compound according to any one of the proceeding Embodiments, wherein $R^5$ represents one of the following formulae:

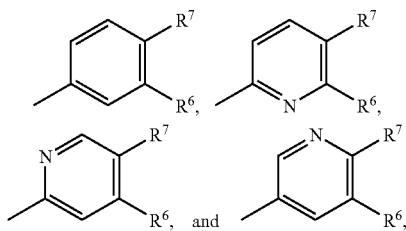

wherein $R^6$ represents halogen, cyano, $C_1$-$C_7$ alkyl, $C_1$-$C_7$ haloalkyl, $C_1$-$C_7$ alkoxy or $C_1$-$C_7$ haloalkoxy; and $R^7$ represents H, $C_1$-$C_7$ alkyl, $C_1$-$C_7$ haloalkyl, $C_1$-$C_7$ alkoxy, $C_1$-$C_7$ haloalkoxy, $C_3$-$C_8$ cycloalkyl, —$SO_2$-$C_3$-$C_8$ cycloalkyl, $C_3$-$C_8$ cycloalkyl-$SO_2$—$R^8$, $C_3$-$C_8$ cycloalkyl, —$SO_2$-$C_3$-$C_8$ cycloalkenyl, $C_3$-$C_8$ cycloalkenyl-$SO_2$—$R^8$, aryl, —$SO_2$-aryl, aryl-$SO_2$—$R^8$, a heterocyclic group, a—$SO_2$-heterocyclic group, a heterocyclic-$SO_2$—$R^8$ group, or —$SO_2$—$NR^9R^{10}$, wherein $R^8$ and $R^9$ each independently represents $C_1$-$C_7$ alkyl or $C_3$-$C_8$ cycloalkyl, and $R^{10}$ represents H, $C_1$-$C_7$ alkyl or $C_3$-$C_8$ cycloalkyl; or $R^6$ and $R^7$ are combined to form a ring together with the carbon atoms to which they are bonded.

Embodiment 14: A compound according to Embodiment 13, wherein the heterocyclic group encompassed by $R^7$ is aromatic, aliphatic or unsaturated.

Embodiment 15: A compound according to Embodiment 13, wherein the heterocyclic group encompassed by $R^7$ is spiro, fused or bridged.

Embodiment 16: A compound according to Embodiment 13, wherein the heterocyclic group encompassed by $R^7$ has 3 to 14 carbon ring atoms, at least one of which is replaced with O, S or $N(R^{03})$ wherein $R^{03}$ represents H, $C_1$-$C_7$ alkyl or $C_3$-$C_8$ cycloalkyl.

Embodiment 17: A compound according to Embodiment 13, wherein the heterocyclic group encompassed by $R^7$ has 1 to 3 rings.

Embodiment 18: A compound according to Embodiment 13, wherein the heterocyclic group encompassed by $R^7$ is selected from the group consisting of aziridinyl, oxiranyl, thiiranyl, azetidinyl, oxetanyl, thietanyl, pyrrolidinyl, tetrahydrofuryl, tetrahydrothienyl, piperidyl, tetrahydropyranyl, tetrahydrothiopyranyl, tetrahydropyridyl, tetrahydroquinolyl, tetrahydroisoquinolyl, morpholinyl, thiomorpholinyl, piperazinyl, dioxolanyl, imidazolidinyl, oxazolidinyl, isoxazolidinyl, thiazolidinyl, pyrazolidinyl, 2H-pyrrolyl, pyrrolinyl, imidazolinyl, pyrazolinyl, dihydrofuryl, dihydrothienyl, dihydropyranyl, dihydrothiopyranyl, dihydropyridyl, dihydroquinolyl, dihydroisoquinolyl, indolinyl, isoindolinyl, furyl, furazanyl, pyranyl, thienyl, pyrrolyl, pyrazolyl, imidazolyl, triazolyl, tetrazolyl, oxazolyl, oxadiazolyl, isoxazolyl, thiazolyl, isothiazolyl, pyridyl, pyridazinyl, pyrimidinyl, pyrazinyl, triazinyl, benzopyranyl, benzofuranyl, indolyl, and quinolinyl.

Embodiment 19: A compound according to any one of the proceeding Embodiments 13 to 18, wherein $R^6$ represents Cl, CN, $CF_3$, or $OCHF_2$.

Embodiment 20: A compound according to Embodiment 19, wherein $R^6$ represents Cl or $CF_3$.

Embodiment 21: A compound according to Embodiment 20, wherein $R^6$ represents $CF_3$.

Embodiment 22: A compound according to any one of the proceeding Embodiments 13 to 21, wherein $R^7$ represents the following formula:

H, $C_1$-$C_7$ alkoxy,

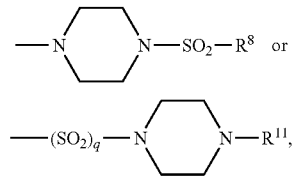

wherein q represents 0 or 1, and $R^{11}$ represents H or $C_1$-$C_7$ alkyl.

Embodiment 23: A compound according to Embodiment 22, wherein $R^7$ represents the following formula:

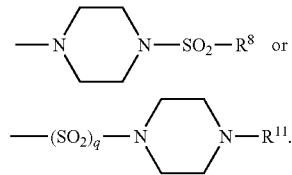

Embodiment 24: A compound according to Embodiment 23, wherein $R^8$ represents methyl or cyclopropyl.

Embodiment 25: A compound according to Embodiment 13, wherein $R^6$ and $R^7$ are combined to form one of the following rings together with the carbon atoms to which they are bonded:

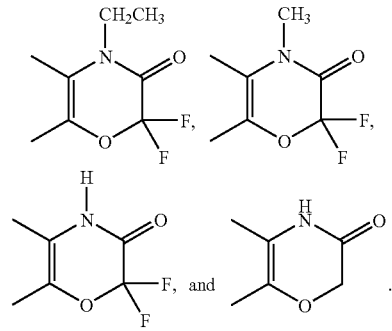

Embodiment 26: A compound according to Embodiment 25, wherein $R^6$ and $R^7$ are combined to form, together with the carbon atoms to which they are bonded,

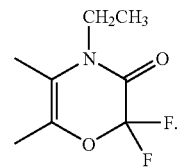

Non-limiting specific examples of the compounds described herein are as follows:

N2-(3-Chloro-4-methoxy)phenyl-5-fluoro-N4-(endo-8-methyl-8-azabicyclo[3.2.1]oct-3-yl)-2,4-pyrimidinediamine

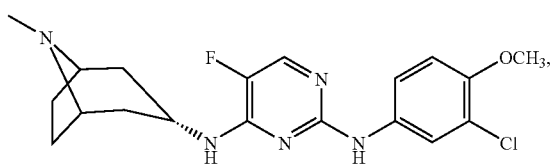

N2-(3-Cyano)phenyl-5-fluoro-N4-(endo-8-methyl-8-azabicyclo[3.2.1]oct-3-yl)-2,4-pyrimidinediamine

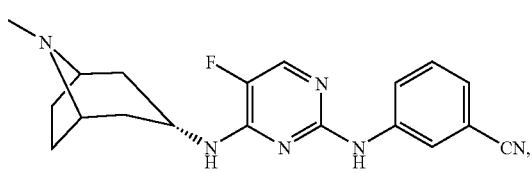

5-Fluoro-N4-(endo-8-methyl-8-azabicyclo[3.2.1]oct-3-yl)-N2-[4-(4-methylsulfonylpiperazino)-3-trifluoromethyl]phenyl-2,4-pyrimidinediamine

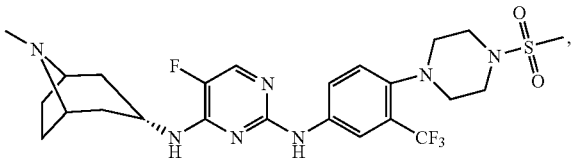

5-Fluoro-N4-(endo-8-methyl-8-azabicyclo[3.2.1]oct-3-yl)-N2-[4-(4-methylpiperazino)-3-trifluoromethyl]phenyl-2,4-pyrimidinediamine

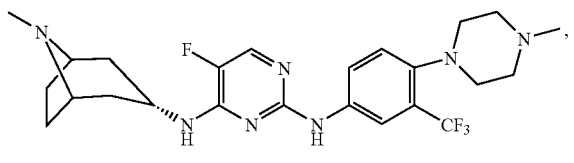

and

N2-[3-Chloro-4-(4-methylsulfonylpiperazino)]phenyl-5-fluoro-N4-(endo-8-methyl-8-azabicyclo[3.2.1]oct-3-yl)-2,4-pyrimidinediamine The compounds described herein preferably do not encompass the following compounds:

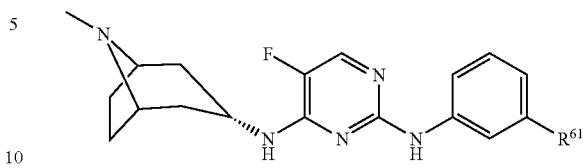

wherein $R^{61}$ represents halogen and in particular, chlorine.

In one of its composition aspects, the present embodiments provide a compound of formula (VI):

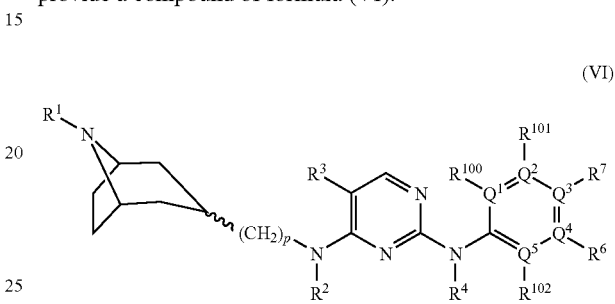

(VI)

wherein
$R^1$ represents H, $C_1$-$C_7$ alkyl or $C_3$-$C_8$ cycloalkyl;
$R^2$ represents H, $C_1$-$C_7$ alkyl or $C_2$-$C_8$ alkanoyl;
$R^3$ represents H, halogen, cyano, nitro, ($C_1$-$C_7$ alkoxy) carbonyl, $C_1$-$C_7$ alkyl, $C_1$-$C_7$ haloalkyl, $C_1$-$C_7$ alkoxy or $C_1$-$C_7$ haloalkoxy;
$R^4$ represents H, $C_1$-$C_7$ alkyl or $C_2$-$C_8$ alkanoyl;
p is 0 or 1;
$Q^1$, $Q^2$, $Q^3$, $Q^4$, and $Q^5$ are independently selected from C and N;
$R^6$, $R^7$, $R^{100}$, $R^{101}$, and $R^{102}$ are independently selected from H, halogen, cyano, $C_1$-$C_7$ alkyl, $C_1$-$C_7$ haloalkyl, $C_1$-$C_7$ alkoxy, $C_1$-$C_7$ haloalkoxy, $C_3$-$C_8$ cycloalkyl, —$SO_2$-$C_3$-$C_8$ cycloalkyl, $C_3$-$C_8$ cycloalkyl-$SO_2$—$R^8$, $C_3$-$C_8$ cycloalkyl, —$SO_2$-$C_3$-$C_8$ cycloalkenyl, $C_3$-$C_8$ cycloalkenyl-$SO_2$—$R^8$, aryl, —$SO_2$-aryl, aryl-$SO_2$—$R^8$, a heterocyclic group, a —$SO_2$-heterocyclic group, a heterocyclic-$SO_2$—$R^8$ group, or —$SO_2$—$NR^9R^{10}$; or
any two of $R^6$, $R^7$, $R^{100}$, $R^{101}$, and $R^{102}$ that are vicinal are combined to form a ring together with the carbon atoms to which they are bonded; and
any of $R^6$, $R^7$, $R^{100}$, $R^{101}$, and $R^{102}$ is absent to satisfy valence requirements;
wherein $R^8$ and $R^9$ each independently represents $C_1$-$C_7$ alkyl or $C_3$-$C_8$ cycloalkyl, and
$R^{10}$ represents H, $C_1$-$C_7$ alkyl or $C_3$-$C_8$ cycloalkyl.

In one of its composition aspects, the present embodiments provide a compound of formula (VII):

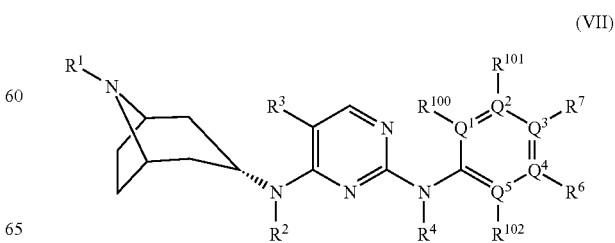

(VII)

wherein $R^1$ represents H, $C_1$-$C_7$ alkyl or $C_3$-$C_8$ cycloalkyl;

$R^2$ represents H, $C_1$-$C_7$ alkyl or $C_2$-$C_8$ alkanoyl;

$R^3$ represents H, halogen, cyano, nitro, ($C_1$-$C_7$ alkoxy) carbonyl, $C_1$-$C_7$ alkyl, $C_1$-$C_7$ haloalkyl, $C_1$-$C_7$ alkoxy or $C_1$-$C_7$ haloalkoxy;

$R^4$ represents H, $C_1$-$C_7$ alkyl or $C_2$-$C_8$ alkanoyl;

$Q^1$, $Q^2$, $Q^3$, $Q^4$, and $Q^5$ are independently selected from C and N;

$R^6$, $R^7$, $R^{100}$, $R^{101}$, and $R^{102}$ are independently selected from H, halogen, cyano, $C_1$-$C_7$ alkyl, $C_1$-$C_7$ haloalkyl, $C_1$-$C_7$ alkoxy, $C_1$-$C_7$ haloalkoxy, $C_3$-$C_8$ cycloalkyl, —$SO_2$-$C_3$-$C_8$ cycloalkyl, $C_3$-$C_8$ cycloalkyl-$SO_2$—$R^8$, $C_3$-$C_8$ cycloalkenyl, —$SO_2$-$C_3$-$C_8$ cycloalkenyl, $C_3$-$C_8$ cycloalkenyl-$SO_2$—$R^8$, aryl, —$SO_2$-aryl, aryl-$SO_2$—$R^8$, a heterocyclic group, a —$SO_2$-heterocyclic group, a heterocyclic-$SO_2$—$R^8$ group, or —$SO_2$—$NR^9R^{10}$; or any two of $R^6$, $R^7$, $R^{100}$, $R^{101}$, and $R^{102}$ that are vicinal are combined to form a ring together with the carbon atoms to which they are bonded; and any of $R^6$, $R^7$, $R^{100}$, $R^{101}$, and $R^{102}$ is absent to satisfy valence requirements;

wherein $R^8$ and $R^9$ each independently represents $C_1$-$C_7$ alkyl or $C_3$-$C_8$ cycloalkyl, and $R^{10}$ represents H, $C_1$-$C_7$ alkyl or $C_3$-$C_8$ cycloalkyl.

In a certain embodiment, the 2,4-pyrimidinediamine compounds described herein can be synthesized from substituted or unsubstituted uracils as illustrated in Scheme I, below.

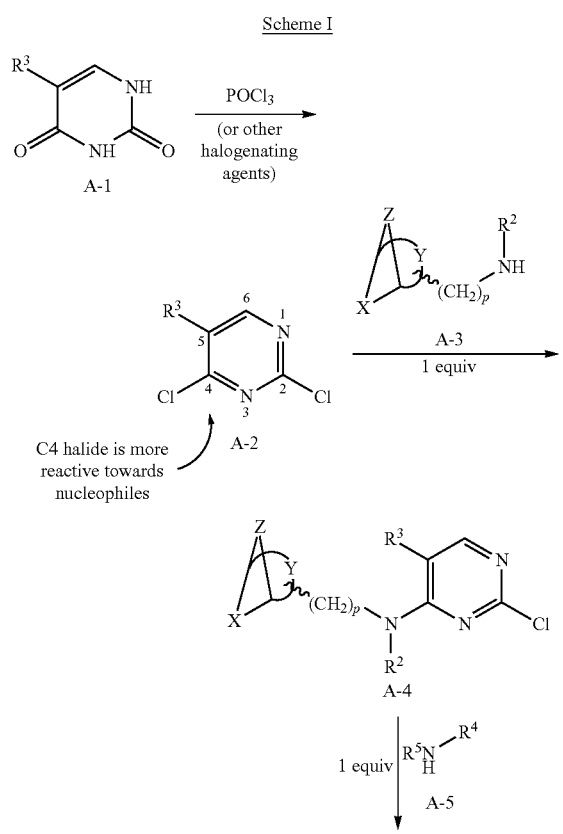

Scheme I

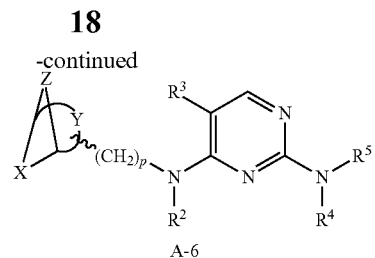

A-6

In Scheme I, X, Y, Z, p, $R^2$, $R^3$, $R^4$ and $R^5$ are the same as defined with respect to formula (I). According to Scheme I, uracil A-1 is dihalogenated at the 2- and 4-positions using a standard dehydrating-halogenating agent such as $POCl_3$ under standard conditions to yield 2,4-dichloropyrimidine A-2. Other halogenating agents, as known to those of skill in the art of organic synthesis, also can be used. Depending upon the nature of the $R^3$ substituent in pyrimidinediamine A-2, the chloride at the C4 position is more reactive towards nucleophiles than the chloride at the C2 position. This differential reactivity can be exploited by first reacting 2,4-dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6, where N4 nitrogen can be selectively alkylated e.g., using an alkylating agent employing a leaving group "LG", to give compounds of formula A-6'.

Typically, the C4 leaving group, such as a halide, is more reactive towards nucleophiles, as illustrated in Scheme I. However, as will be recognized by skilled artisans, the identity of the $R^3$ substituent may alter this reactivity. For example, when $R^3$ is trifluoromethyl, a 50:50 mixture of 4N-substituted-4-pyrimidineamine A-4 and the corresponding 2N-substituted-2-pyrimidineamine is typically obtained. The regioselectivity of the reaction can also be controlled by adjusting the solvent and other synthetic conditions (such as temperature), as is well-known in the art.

The reactions depicted in Scheme I may proceed more quickly when the reaction mixtures are heated via microwave. When heating in this fashion, the following conditions can be used: heat to 175° C. in ethanol for 5-20 min. in a Smith Reactor (Personal Chemistry, Uppsala, Sweden) in a sealed tube (at 20 bar pressure).

The uracil A-1 starting materials can be purchased from commercial sources or prepared using standard techniques of organic chemistry. Commercially available uracils that can be used as starting materials in Scheme I include, by way of example and not limitation, uracil (Aldrich #13,078-8; CAS Registry 66-22-8); 5 bromouracil (Aldrich #85,247-3; CAS Registry 51-20-7; 5 fluorouracil (Aldrich #85,847-1; CAS Registry 51-21-8); 5 iodouracil (Aldrich #85,785-8; CAS Registry 696-07-1); 5 nitrouracil (Aldrich #85,276-7; CAS Registry 611-08-5); 5 (trifluoromethyl)-uracil (Aldrich #22, 327-1; CAS Registry 54-20-6). Additional 5-substituted uracils are available from General Intermediates of Canada, Inc., Edmonton, Calif. and/or Interchim, Cedex, France, or can be prepared using standard techniques. A myriad of textbook references teaching suitable synthetic methods for 5-substituted uracils are disclosed herein.

Amines A-3 and A-5 can be purchased from commercial sources or, alternatively, can be synthesized utilizing standard techniques. For example, suitable amines can be synthesized from nitro precursors using standard chemistry. See also Vogel, 1989, Practical Organic Chemistry, Addison Wesley Longman, Ltd. and John Wiley & Sons, Inc. Examples of suitable A-3 amines for use in the synthesis of the presently disclosed compounds include, without limitation, the following:

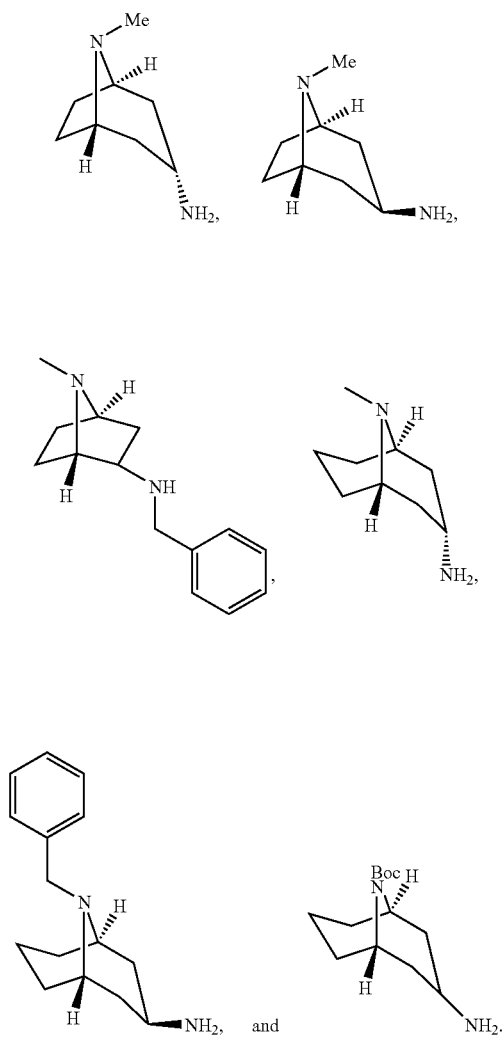

Additional examples of suitable A-3 amines for the preparation of the presently disclosed compounds will be readily apparent to those of skill in the art upon consideration of the present disclosure and can be synthesized as is known to those of ordinary skill in the art or purchased from commercial sources. Examples of such A-3 amines are available from Aldrich, Milwaukee, Wis.; additional suppliers can be identified through the Available Chemical Directory.

Skilled artisans will recognize that in some instances, amines A-3 and A-5 and/or substituent $R^3$ on uracil A-1 include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, *Protective Groups in Organic Synthesis,* 3d Edition, John Wiley & Sons, Inc., New York (1999) and the references cited therein (hereinafter "Greene & Wuts").

A specific embodiment of Scheme I utilizing 5-fluorouracil (Aldrich #32,937-1) as a starting material is illustrated in Scheme Ia, below.

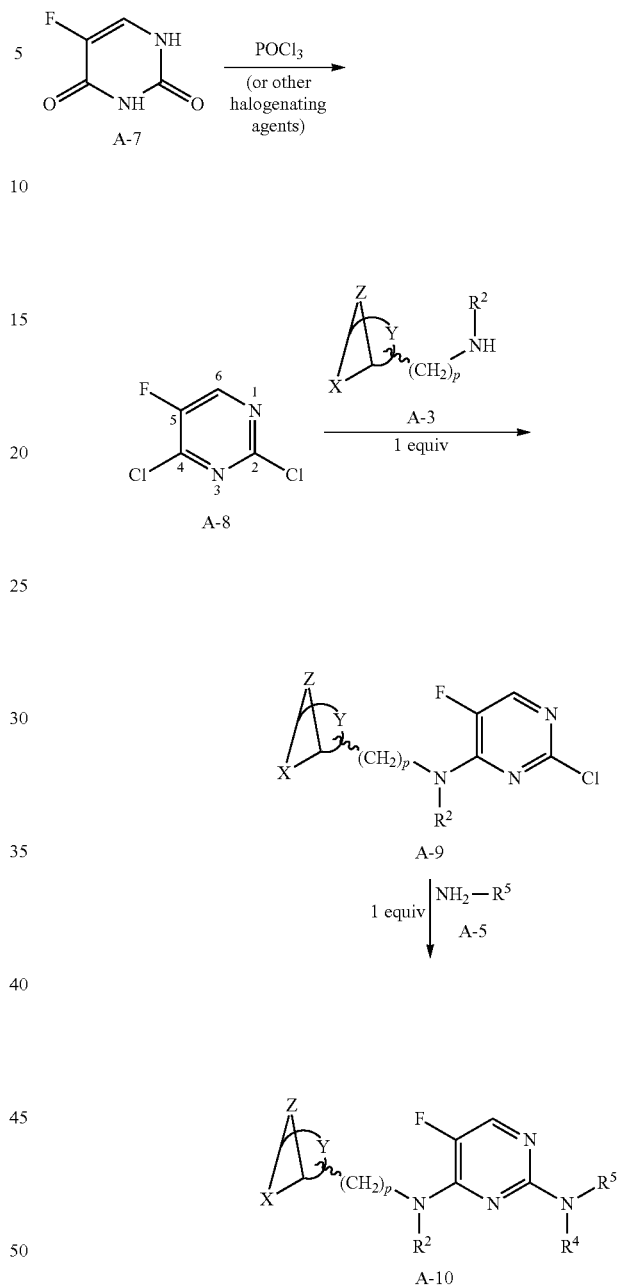

In Scheme Ia, X, Y, Z, p, $R^2$, and $R^5$ are the same as defined with respect to Scheme I. Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-9) followed by one or more equivalents of amine A-5.

In a certain embodiment, the 2,4-pyrimidinediamine compounds described herein can be synthesized from substituted or unsubstituted cytosines as illustrated in Schemes IIa and IIb, below.

Scheme IIa

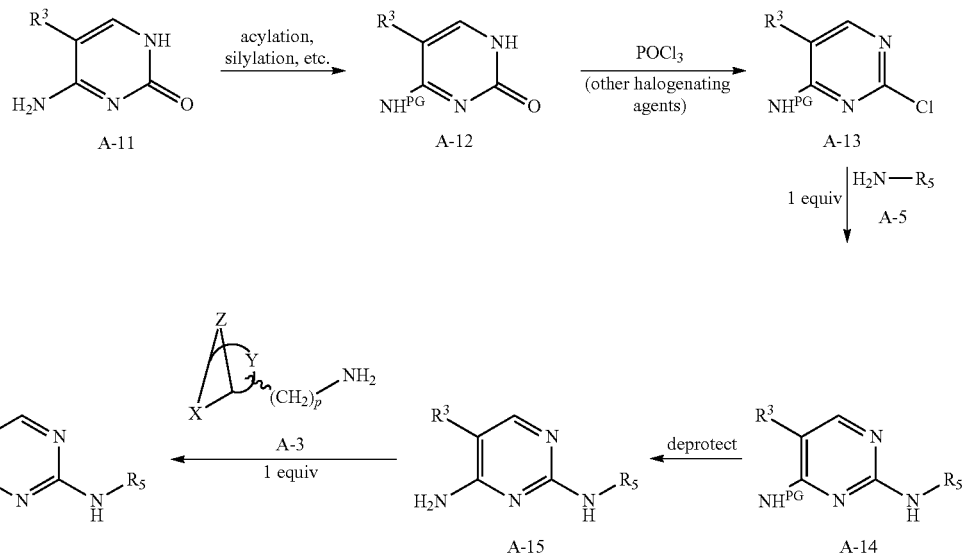

In Scheme IIa, X, Y, Z, p, R³, and R⁵ are the same as defined with respect to Scheme I, and PG represents a protecting group. Referring to Scheme IIa, the C4 exocyclic amine of cytosine A-11 is first protected with a suitable protecting group PG to yield N4-protected cytosine A-12. For specific guidance regarding protecting groups useful in this context, see Vorbrüggen and Ruh-Pohlenz, 2001, Handbook of Nucleoside Synthesis, John Wiley & Sons, NY, pp. 1-631 ("Vorbrüggen"). Protected cytosine A-12 is halogenated at the C2 position using a standard halogenation reagent under standard conditions to yield 2-chloro-4N-protected-4-pyrimidineamine A-13. Reaction with amine A-5 gives A-14, which on deprotection of the C4 exocyclic amine, gives A-15. Reaction of A-15 with amine A-3 yields 2,4-pyrimidinediamine derivative A-6.

Scheme IIb

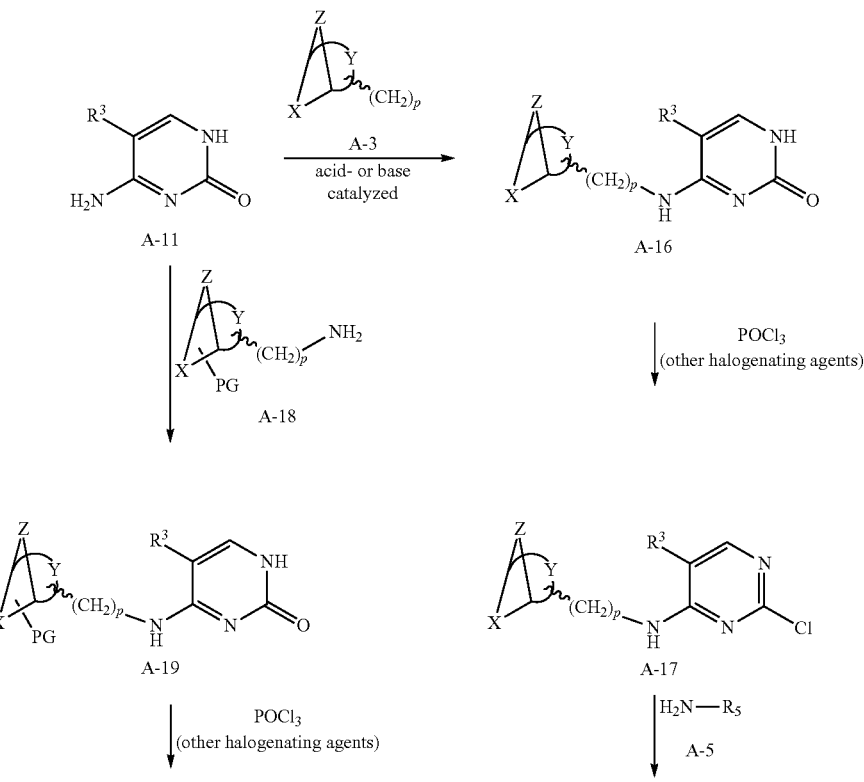

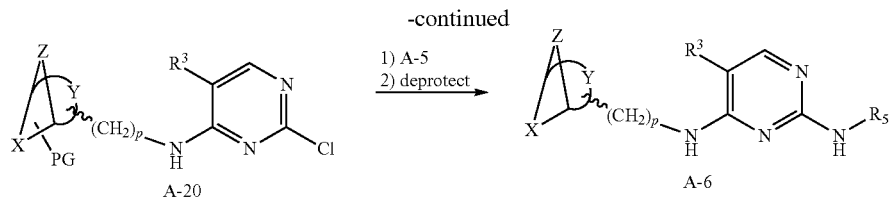

In Scheme IIb, X, Y, Z, p, $R^3$, and $R^5$ are the same as previously defined with respect to Scheme I and PG represents a protecting group. Referring to Scheme IIb, cytosine A-11 can be reacted with amine A-3 or protected amine A-18 to yield N4-substituted cytosine A-16 or A-19, respectively. These substituted cytosines can then be halogenated as previously described, deprotected (in the case of N4-substituted cytosine A-19) and reacted with amine A-5 to yield a 2,4-pyrimidinediamine A-6.

Commercially available cytosines that can be used as starting materials in Schemes IIa and IIb include, but are not limited to, cytosine (Aldrich #14,201-8; CAS Registry 71-30-7); N4-acetylcytosine (Aldrich #37,791-0; CAS Registry 14631-20-0); 5 fluorocytosine (Aldrich #27,159-4; CAS Registry 2022-85-7); and 5-(trifluoromethyl)-cytosine. Other suitable cytosines useful as starting materials in Schemes IIa are available from General Intermediates of Canada, Inc., Edmonton, Calif. and/or Interchim, Cedex, France, or can be prepared using standard techniques. A myriad of textbook references teaching suitable synthetic methods are provided infra herein.

In a certain embodiment, the 2,4-pyrimidinediamine compounds described herein can be synthesized from substituted or unsubstituted 2-amino-4-pyrimidinols as illustrated in Scheme III, below.

Suitable commercially available 2-amino-4-pyrimidinols A-21 that can be used as starting materials in Scheme III are available from General Intermediates of Canada, Inc., Edmonton, Calif. and/or Interchim, Cedex, France, or can be prepared using standard techniques. A myriad of textbook references teaching suitable synthetic methods are provided infra herein.

References teaching methods useful for synthesizing pyrimidines generally, as well as starting materials described in Schemes I-III, are known in the art. For specific guidance, the reader is referred to Brown, D. J., "The Pyrimidines", in The Chemistry of Heterocyclic Compounds, Volume 16 (Weissberger, A., Ed.), 1962, Interscience Publishers, (A Division of John Wiley & Sons), New York ("Brown I"); Brown, D. J., "The Pyrimidines", in The Chemistry of Heterocyclic Compounds, Volume 16, Supplement I (Weissberger, A. and Taylor, E. C., Ed.), 1970, Wiley-Interscience, (A Division of John Wiley & Sons), New York (Brown II"); Brown, D. J., "The Pyrimidines", in The Chemistry of Heterocyclic Compounds, Volume 16, Supplement II (Weissberger, A. and Taylor, E. C., Ed.), 1985, An Interscience Publication (John Wiley & Sons), New York ("Brown III"); Brown, D. J., "The Pyrimidines" in The Chemistry of Heterocyclic Compounds, Volume 52 (Weissberger, A. and Taylor, E. C., Ed.), 1994, John Wiley & Sons, Inc., New York, pp. 1-1509 (Brown IV"); Kenner, G. W.

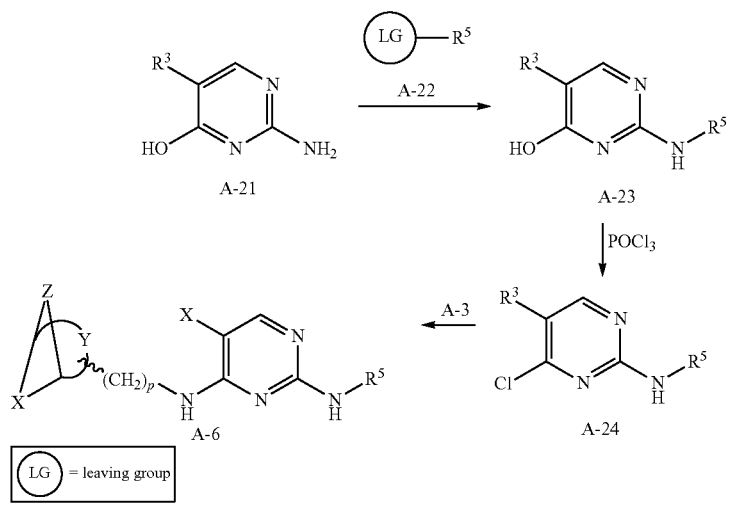

Scheme III

In Scheme III, X, Y, Z, p, $R^3$, and $R^5$ are the same as previously defined with respect to Scheme I and LG is a leaving group. Referring to Scheme III, 2-amino-4-pyrimidinol A-21 is reacted with arylating agent A-22 to yield N2-substituted-4-pyrimidinol A-23, which is then halogenated as previously described to yield N2-substituted-4-halo-2-pyrimidineamine A-24. Further reaction with amine A-3 affords a 2,4-pyrimidinediamine derivative A-6.

and Todd, A., in Heterocyclic Compounds, Volume 6, (Elderfield, R. C., Ed.), 1957, John Wiley, New York, Chapter 7 (pyrimidines); Paquette, L. A., Principles of Modern Heterocyclic Chemistry, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., Heterocyclic Chemistry, 3rd Edition, 1995, Chapman and Hall, London, UK, pp. 1-516; Vorbrüggen, H. and Ruh-Pohlenz, C., Handbook of Nucleoside Synthesis, John Wiley & Sons, New York, 2001, pp. 1-631 (protection of pyrimidines by acylation pp. 90-91; silylation of pyrimidines pp. 91-93); Joule, J. A., Mills, K. and Smith, G. F., Heterocyclic Chemistry, 4th Edition, 2000, Blackwell Science, Ltd, Oxford, UK, pp. 1-589; and Comprehensive Organic Synthesis, Volumes 1-9 (Trost, B. M. and Fleming, I., Ed.), 1991, Pergamon Press, Oxford, UK.

It has been discovered that 2,4-pyrimidinediamine compounds described herein modulate the activity of certain cytokines and can be used to treat an inflammatory disease in a subject. Certain compounds disclosed herein elevate the production of anti-inflammatory cytokines and/or decrease the production of pro-inflammatory cytokines. Such compounds are useful in treating a variety of inflammatory conditions, examples of which are discussed below. In one aspect, compounds elevate the production of IL-10, an anti-inflammatory cytokine. Other disclosed compounds inhibit IL-23 production. The pro-inflammatory effect of IL-23 has been well documented and anti-IL-23 antibody therapy currently is being used in the treatment of various inflammatory and autoimmune disorders. Certain embodiments of the disclosed compounds both boost IL-10 production and inhibit IL-23 production. In one embodiment the disclosed compounds boost IL-10 production at a concentration where they inhibit IL-23 production. In certain embodiments the disclosed compounds inhibit IL-23 production in response to an inflammatory stimulus. For example, such IL-23 inhibitory compounds may inhibit IL-23 production with an inhibitory concentration ($IC_{50}$) value of less than about 0.01 µM, or even less than about 1 nM, to about 20 µM, such as from about 0.1 µM to about 10 µM or from about 0.05 µM to about 2 µM. Disclosed compounds that boost IL-10 production typically raise IL-10 levels from less than 2-fold—such as by about 10% to about 30% or from about 20% to about 90%—to about 10-fold. Certain examples of these compounds do not significantly inhibit IL-23, but exert their anti-inflammatory effect primarily by increasing IL-10 production. In certain embodiments, compounds that increase IL-10 production also increase IL-23 production. Such compounds may also be anti-inflammatory if the compounds increase IL-10 production more effectively than they increase IL-23 production. Compounds disclosed herein that raise IL-10 levels typically raise IL-10 levels with an $EC_{50}$ of from about 0.01 µM, or even less than about 1 nM, to about 20 µM, such as from about 0.1 µM to about 10 µM or from about 0.05 µM to about 1 µM.

In certain embodiments, compounds that inhibit IL-23 production also boost IL-10 production. However, certain disclosed compounds may inhibit both IL-23 production and IL-10 production. Typically such compounds also are considered to be anti-inflammatory. For example, in certain embodiments, disclosed anti-inflammatory compounds inhibit IL-23 production more effectively than they inhibit IL-10 production, for example from about 2-fold to about 10-fold more effectively, such as from about 2-fold to about 5-fold more effectively. In other embodiments, the anti-inflammatory compounds inhibit IL-23 production as effectively as they inhibit IL-10, yet still exert an overall anti-inflammatory effect.

Standard physiological, pharmacological and biochemical procedures are available for testing the compounds provided herein to identify those that possess anti-inflammatory activity. In vitro and in vivo assays that may be used to evaluate the anti-inflammatory activity are known to those of skill in the art. Procedures suitable for testing the IL-23 inhibitory and IL-10 boosting activity of the compounds are also available, and examples of such procedures are described herein.

The term "inflammatory disorder" or "inflammatory disease" is used to refer to abnormalities associated with inflammation, and comprises a large group of disorders. An inflammatory disorder can be associated with acute inflammation and/or chronic inflammation.

Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barre, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; autoimmune conditions; proliferative disorders (including Kaposi's sarcoma and other proliferative disorders of smooth muscle cells); inflammatory bowel diseases (including ulcerative colitis and Crohn's disease); allergic reactions; inflammatory myopathies (including as dermatomyositis, polymyositis, and inclusion body myositis); and leukocyte defects (including Chediak-Higashi syndrome and chronic granulomatous disease).

Respiratory Disorders

Respiratory disorders that may be treated include a disease or disorder of the respiratory system that can affect any part of the respiratory tract. Certain diseases cause respiratory symptoms although the diseases are initially caused by an infection, such as a cold virus, bronchitis, pneumonia and tuberculosis. Other disorders are caused by irritation of the lung tissue, such as, for example, by an allergen. These disorders include hay fever and other respiratory allergies and asthma. In certain embodiments, the host is at risk of or suffering from a disorder of the lower airway. These include bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis.

In asthma, the bronchi and bronchioles are typically temporarily constricted and inflamed. Other disorders typically involving lung irritants include emphysema, which can result from multiple factors including: smog, cigarette smoke, infection, and a genetic predisposition to the condition, laryngitis, lung cancer, respiratory distress syndrome (RDS), which refers to a group of symptoms that indicate severe malfunctioning of the lungs affecting adults and infants and specifically Adult respiratory distress syndrome (ARDS). Chronic respiratory insufficiency (or chronic obstructive pulmonary disease; COPD) is a prolonged or persistent condition characterized by breathing or respiratory dysfunction resulting in reduced rates of oxygenation or the ability to eliminate carbon dioxide.

The term "asthma" as used herein includes any asthmatic condition marked by recurrent attacks of paroxysmal dyspnea (i.e., "reversible obstructive airway passage disease") with wheezing due to spasmodic contraction of the bronchi (so called "bronchospasm"). Asthmatic conditions which may be treated or even prevented in accordance with the embodiments include allergic asthma and bronchial allergy characterized by manifestations in sensitized persons provoked by a variety of factors including exercise, especially vigorous exercise ("exercise-induced bronchospasm"), irritant particles (pollen, dust, cotton, cat dander) as well as mild to moderate asthma, chronic asthma, severe chronic asthma, severe and unstable asthma, nocturnal asthma, and psychologic stresses.

Other respiratory disorders include allergic and non-allergic rhinitis as well as non-malignant proliferative and/or inflammatory disease of the airway passages and lungs. Allergic rhinitis means generally any allergic reaction of the nasal mucosa and includes hay fever (seasonal allergic rhinitis) and perennial rhinitis (non-seasonal allergic rhinitis) which are characterized by seasonal or perennial sneezing, rhinorrhea, nasal congestion, pruritis and eye itching, redness and tearing. Non-allergic rhinitis means eosinophilic nonallergic rhinitis which is found in patients with negative skin tests and those who have numerous eosinophils in their nasal secretions.

Non-malignant proliferative and/or inflammatory diseases of the airway passages or lungs means one or more of (1) alveolitis, such as extrinsic allergic alveolitis, and drug toxicity such as caused by, e.g., cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In one embodiment, the use of the compounds of the embodiments reduces symptoms of these disorders, including cough, shortness of breath, chest pain, wheezing, cyanosis, finger clubbing, stridor (a crowing sound when breathing), hemoptysis (coughing up of blood), and respiratory failure. The use of these compounds may reduce respiratory acidosis, due to a failure by the lungs to remove carbon dioxide.

In another embodiment, the use of the compounds improves lung function.

Cardiovascular Related Disorders

In one embodiment, the compounds of the embodiments are administered to a patient suffering from a cardiovascular disorder related to inflammation. These include, but are not limited to, atherosclerosis, post-angioplasty restenosis, coronary artery diseases and angina.

Generally, cardiovascular disorders are a class of diseases that involve the heart and/or blood vessels (arteries and veins). While the term technically refers to any disease that affects the cardiovascular system, it is usually used to refer to those related to atherosclerosis (arterial disease).

Cardiovascular inflammatory disorders include atherosclerosis, post-angioplasty, restenosis, coronary artery diseases, angina, and other cardiovascular diseases. In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes. In an alternative embodiment, the compounds can be administered to treat small vessel disease that is not treatable by surgery or angioplasty, or other vessel disease in which surgery is not an option. The compounds can also be used to stabilize patients prior to revascularization therapy.

Generally, unstable atherosclerotic plaque is a result of multiple factors but is commonly characterized by an infiltrate of inflammatory cells. Medical research strongly supports a role for inflammation in the pathogenesis, progression, and disruption of atherosclerotic plaque. Clinical studies have demonstrated systemic markers of inflammation to be strong predictors of clinical events, and specific treatments of atherosclerosis and its risk factors have been associated with reductions in inflammatory markers. The majority of cardiovascular events occur at sites of "nonsignificant" stenosis, as inflammation can lead to instability and rupture of these smaller atherosclerotic plaques, which are more numerous than the "significant," flow-limiting plaques. In fact, direct visualization of inflammatory cells within plaques is a predictor of unstable coronary disease. The source of inflammation is uncertain; various infectious agents have been proposed as a stimulator of this inflammatory process. Smooth muscle cell proliferation is also implicated both in chronic cardiovascular pathologies such as atherosclerosis, and more directly in, for example, post-angioplasty restenosis.

Diseases of arteries, arterioles and capillaries generally include atherosclerosis, peripheral vascular diseases including Raynaud's syndrome, thromboangiitis obliterans (Buerger) and other specified peripheral vascular diseases such as intermittent claudication.

Proliferative Disorders

Chronic inflammation is a risk factor for many proliferative disorders. For example, in a variety of diseases, airway smooth muscle mass increases due to the coordinated increase in size (hypertrophy) and number (hyperplasia) of airway smooth muscle cells. Myocyte migration may also serve to regulate airway smooth muscle mass. For example, chronic cellular inflammation and airway wall remodeling with subepithelial fibrosis and airway smooth muscle (ASM) cell hyperplasia are features of chronic asthma. In addition, vascular smooth muscle, and immune cells are stimulated in cardiovascular disorders.

In particular, inflammation is a risk factor in development of cancers, including colon cancer, and data from experimental and observational studies suggest that inflammation acts early in the carcinogenic pathway of colorectal cancer, possibly promoting the progression of colorectal adenomas to adenocarcinoma.

Other Inflammatory Disorders

In another embodiment, the compounds of the embodiments may be administered for the treatment or prophylaxis of an inflammatory disorder or the joints or connective tissue. These disorders include rheumatoid arthritis, lupus erythematosus, Sjogren's syndrome, scleroderma (systemic sclerosis), dermatomyositis, polychondritis, polymyositis, polymyalgia rheumatica, osteoarthritis, septic arthritis, fibromyalgia, gout, pseudogout, spondyloarthropathies, such as ankylosing spondylitis, reactive arthritis (Reiter's syndrome), psoriatic arthropathy, enteropathic spondylitis and reactive arthropathy, vasculitis, such as polyarteritis nodosa, Henoch-Schonlein purpura, serum sickness, Wegener's granulomatosis, giant cell arteritis, temporal arteritis, Takayasu's arteritis, Behccet's syndrome, Kawasaki's disease (mucocutaneous lymph node syndrome) and Buerger's disease (thromboangiitis obliterans). In addition, autoimmune conditions such as acute disseminated encephalomyelitis, Addison's disease, ankylosing spondylitisis, antiphospholipid antibody syndrome, autoimmune hepatitis, Coeliac disease, Crohn's disease, diabetes mellitus, Graves' disease, Guillain-Barre syndrome, Hashimoto's disease, idiopathic thrombocytopenic purpura, Kawasaki's Disease, lupus erythematosus, multiple sclerosis, Mmyasthenia gravis, opsoclonus myoclonus syndrome, optic neuritis, Ord's thyroiditis, pemphigus, pernicious anaemia, primary biliary cirrhosis, Reiter's syndrome, Sjogren's syndrome, Takayasu's arteritis, temporal arteritis, warm autoimmune hemolytic anemia and Wegener's granulomatosis.

In other embodiments, certain inflammatory skin disorders are treated, such as dermatitis, eczematous dermatitis and psoriasis. In general inflammatory skin disease is a broad category that includes many conditions, ranging in severity from mild itching to serious medical health complications. Other conditions that are inflammatory skin disorders include eczema generally, acne and rosacea.

Other disorders may also be treated by administration of compounds of the embodiments. In certain embodiments, the disorder to be treated is selected from post transplantation late and chronic solid organ rejection; multiple sclerosis; autoimmune conditions (including systemic lupus erythematosus, dermatomyositis, polymyositis, inflammatory neuropathies (Guillain Barre, inflammatory polyneuropathies), vasculitis (Wegener's granulomatosus, polyarteritis nodosa), and rare disorders such as polymyalgia rheumatica, temporal arteritis, Sjogren's syndrome, Bechet's disease, Churg-Strauss syndrome, and Takayasu's arteritis).

Diabetes

In another embodiment, the compounds of the embodiments may be administered for the treatment prophylaxis or delay of onset of diabetes, pre-diabetes and related disorders. Related disorders of diabetes include, but are not limited to, hyperglycemia, abnormal glucose homeostasis, insulin resistance, Syndrome X, metabolic disorders, diabetic dyslipidemia. In one embodiment, the disease to be treated or prevented is type 2 diabetes. In one embodiment, patients at risk for developing diabetes are prophylactically treated to prevent onset. Patients with diabetes or at risk for developing diabetes can be identified through several risk factors. One of the key risk factors is age and obesity. Generally patients who are 45 years or older and overweight (with a body mass index of 25 or greater) is at risk of developing diabetes.

Inflammatory arthritis comprises a condition where arthritis is present because of localized joint inflammation. Rheumatoid arthritis, generally considered a type of inflammatory arthritis, involves many joints all of which are damaged to some degree by inflammation and its sequelae. Osteoarthritis, also known as "degenerative arthritis" or "degenerative joint disease," is a clinical syndrome in which low-grade inflammation results in pain in the joints, caused by abnormal wearing of the cartilage that covers and acts as a cushion inside joints and destruction or decrease of synovial fluid that lubricates those joints. In certain embodiments, the inflammatory disorder described herein is an inflammatory arthritis, including but not limited to rheumatoid arthritis or osteoarthritis. Psoriasis comprises a non-contagious disorder which affects the skin and joints. The scaly skin patches caused by psoriasis, called psoriatic plaques, are areas of inflammation and excessive skin production. In certain embodiments, the inflammatory disorder described herein is psoriasis.

The terms "treating," "treatment," and the like are used herein to generally mean obtaining a desired pharmacological and physiological effect, and refer to complete elimination as well as to any clinically or quantitatively measurable reduction in the inflammatory condition for which the subject is being treated. "Treatment" is an intervention performed for preventing the development or altering the pathology or symptoms of a disorder. Accordingly, "treatment" refers to both therapeutic treatment and prophylactic or preventative measures. "Treatment" may also be specified as palliative care.

More specifically, 2,4-pyridinediamine compounds described herein which are used to treat a subject with an inflammatory disorder are provided in a therapeutically effective amount to prevent the disorder (i.e., inhibit the onset or occurrence of the disorder and/or cause the clinical symptoms of the disorder not to develop in a mammal that may be exposed to or predisposed to the disorder but does not yet experience or display symptoms of the disorder); inhibit the disorder (i.e., arrest or reduce the development of the disorder or its clinical symptoms); or relieve the disorder (i.e., cause regression of the disorder or its clinical symptoms). Subjects in need of treatment include those already with one or more inflammatory disorder as well as those in which one or more inflammatory disorder is to be prevented.

A "subject in need thereof" refers to any subject or individual who could benefit from the method of treatment described herein. In certain embodiments, a subject in need thereof is a subject predisposed for the development of one or more inflammatory disorders; a subject having one or more inflammatory disorders but not exhibiting any clinical symptoms; or a subject having one or more inflammatory disorders and exhibiting symptoms of the one or more inflammatory disorders. The "subject in need thereof" refers to a vertebrate, such as a mammal. Mammals include, but are not limited to, humans, other primates, rodents (i.e., mice, rats, and hamsters), farm animals, sport animals and pets. In one embodiment, the subject is a mammal such as a human. In certain embodiments, the methods find use in experimental animals, in veterinary application, and/or in the development of animal models for disease.

As used herein, the term "administering" or "introducing" a compound to a subject means providing the compound to a subject. Methods of administering to subjects include any of a number of convenient means including, but not limited to, systemic administration (e.g., intravenous injection, intraparenteral injection, inhalation, transdermal delivery, oral delivery, nasal delivery, rectal delivery, etc.) and/or local administration (e.g., direct injection into a target tissue, delivery into a tissue via cannula, delivery into a target tissue by implantation of a time-release material, or delivery through the skin via a topical composition such as a cream, lotion, or the like), delivery into a tissue by a pump, etc., intraosseously, in the cerebrospinal fluid, or the like. "Orally delivery" refers to administration in an oral form, such as in a pharmaceutically acceptable carrier and/or diluent. Oral delivery includes ingestion of the compound as well as oral gavage of the drug.

Further modes of administration include buccal, sublingual, vaginal, subcutaneous, intramuscular, intradermal, and aerosol administration.

Modes of administration can include delivery via a sustained release and/or controlled release drug delivery formulation and/or device. "Sustained release" refers to release of a drug or an active metabolite thereof into the systemic circulation over a prolonged period of time relative to that achieved by oral administration of a conventional formulation of the drug. "Controlled release" is a zero order release; that is, the drug releases over time irrespective of concentration. Single, multiple, continuous or intermittent administration can be effected.

In one embodiment, a composition comprising one or more 2,4-pyrimidinediamine compounds described herein is administered orally to a subject having an inflammatory arthritis such as osteoarthritis. In another embodiment, a composition comprising one or more 2,4-pyrimidinediamine compounds described herein is injected directly into an affected joint of a subject having an inflammatory arthritis such as osteoarthritis. In yet another embodiment, a composition comprising one or more 2,4-pyrimidinediamine compounds described herein is administered via a topical formulation applied to the skin proximal to an affected joint of a subject having an inflammatory arthritis such as osteoarthritis arthritis.

A "therapeutically effective amount" or "pharmaceutically effective amount" means the amount of 2,4-pyrimidinediamine compound described herein that, when administered to a subject for treating an inflammatory disorder, is sufficient to effect such treatment for the disorder. Thus, a "therapeutically effective amount" is an amount indicated for treatment while not exceeding an amount which may cause significant adverse effects (at a reasonable benefit/risk ratio) within the scope of sound medical judgment. The "therapeutically effective amount" will vary depending on the compound, and will also be determined by physical and physiological factors such the disorder and its severity, and the age, body weight, and/or clinical history of the subject to be treated. Methods for evaluating the effectiveness of therapeutic treatments are known to those of skill in the art.

Doses to be administered are variable according to the treatment period, frequency of administration, the host, and the nature and severity of the disorder. The dose can be determined by one of skill in the art without an undue amount of experimentation. The 2,4-pyrimidinediamine compounds described herein are administered in dosage concentrations sufficient to ensure the release of a sufficient dosage unit into the patient to provide the desired treatment of the inflammatory disorder. The active ingredients may be administered to achieve therapeutic or prophylactic blood concentrations, such as in vivo plasma concentrations of the 2,4-pyrimidinediamine compounds described herein of from about 0.01 to about 10,000 ng/cc, such as from about 0.01 to about 1,000 ng/cc.

"Therapeutic or prophylactic blood concentrations" refers to systemic exposure to a sufficient concentration of a compound or an active metabolite thereof over a sufficient period of time to effect disease therapy or to prevent the onset or reduce the severity of a disease in the treated animal.

For example, the methods described herein may use compositions to provide from about 0.01 to about 100 mg/kg body weight/day of the 2,4-pyrimidinediamine compounds described herein, from about 0.01 to about 10 mg/kg body weight/day of the compounds, or about 30 mg/kg body weight/day of the compounds. It will be understood, however, that dosage levels that deviate from the ranges provided may also be suitable in the treatment of a given disorder.

The 2,4-pyrimidinediamine compounds described herein may be in any form suitable for administration. Such administrable forms include tablets, buffered tablets, pills, capsules, enteric-coated capsules, dragees, cachets, powders, granules, aerosols, liposomes, suppositories, creams, lotions, ointments, skin patches, parenterals, lozenges, oral liquids such as suspensions, solutions and emulsions (oil-in-water or water-in-oil), ophthalmic liquids and injectable liquids, or sustained- and/or controlled release forms thereof. The desired dose may be provided in several increments at regular intervals throughout the day, by continuous infusion, or by sustained and/or controlled release formulations, or may be presented as a bolus, electuary or paste.

"Practical dosage regimen" refers to a schedule of drug administration that is practical for a patient to comply with. For human patients, a practical dosage regimen for an orally administered drug is likely to be an aggregate dose of less than 10 g/day.

In one embodiment, a pharmaceutical composition or formulation comprising one or more 2,4-pyrimidinediamine compounds described herein is prepared by admixture with one or more pharmaceutically acceptable carriers. Other products may be added, if desired, to maximize compound preservation, or to optimize a particular method of delivery. In addition, the present methods include use of combination compositions comprising the 2,4-pyrimidinediamine compounds described herein as described herein in conjunction (combination or alternation) with other agents suitable for the treatment of inflammatory disorders. In certain embodiments, the combination or alternation can be synergistic.

"Pharmaceutically acceptable carrier" or "diluent" means a carrier that is useful in preparing a pharmaceutical composition that is generally safe, neither biologically nor otherwise undesirable, not toxic or otherwise unacceptable commensurate with a reasonable benefit/risk ratio, compatible with other ingredients of the formulation, and includes a carrier that is acceptable for veterinary use as well as human pharmaceutical use. "A pharmaceutically acceptable carrier" as used in the specification and claims includes both one and more than one such carrier.

A "pharmaceutically acceptable carrier" includes any and all solvents, dispersion media, coatings, antibacterial and anti-fungal agents, isotonic and absorption delaying agents, and the like, compatible with pharmaceutical administration of a composition comprising one or more 2,4-pyrimidinediamine compounds described herein. Examples of such carriers or diluents include, but are not limited to, water, saline, Ringer's solutions and dextrose solution. The volume of the pharmaceutical composition is based on the intended mode of administration and the safe volume for the individual patient, as determined by a medical professional.

The present embodiments relate to use of the 2,4-pyrimidinediamine compounds described herein for the manufacture of a medicament.

The foregoing disclosure is further described in the following non-limiting examples. In the examples below as well as throughout the application, the following abbreviations have the following meanings. If not defined, the terms have their generally accepted meanings.

mL=milliliter
s=singlet
d=doublet
t=triplet
q=quartet
m=multiplet
dd=doublet of doublets
br=broad
nM=nanomolar
μg=microgram
ng=nanogram
MS=mass spectrum or mass spectrometry
LC=liquid chromatography
DMSO=dimethylsulfoxide
μL=microliter
mM=millimolar
rpm=revolutions per minute

EXAMPLES

Example 1

Synthesis of 5-fluoro-N4-(endo-8-methyl-8-azabicyclo[3.2.1]oct-3-yl)-N2-[4-(4-methylsulfonylpiperazino)-3-trifluoromethyl]phenyl-2,4-pyrimidinediamine

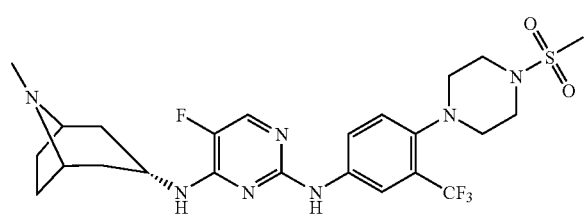

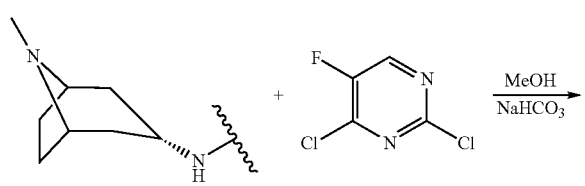

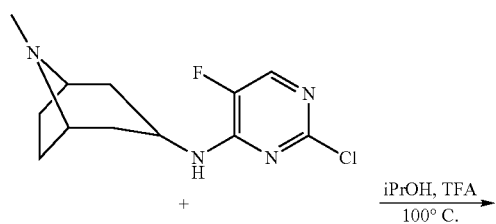

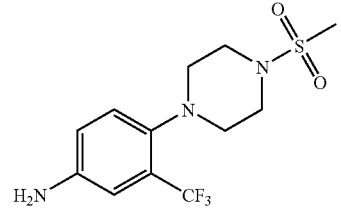

Endo-3-aminotropane.2HCl (500 mg), 2,4-dichloro-5-fluoropyrimidine (750 mg) and NaHCO$_3$ (394 mg) were dissolved in methanol (5 mL). The reaction solution was stirred at room temperature overnight. The reaction solution was evaporated and crystallized from ethyl acetate and hexanes to give 2-chloro-5-fluoro-N4-(endo-8-methyl-8-azabicyclo[3.2.1]oct-3-yl)-4-pyrimidineamine HCl salt. $^1$H NMR (DMSO-d$_6$): δ 1.91-2.20 (m, 10H), 2.63 (s, 3H), 4.22 (br, 1H), 8.09 (d, J=3.3 Hz, 1H), 8.30 (br, 1H), 10.66 (br, 1H) ppm.

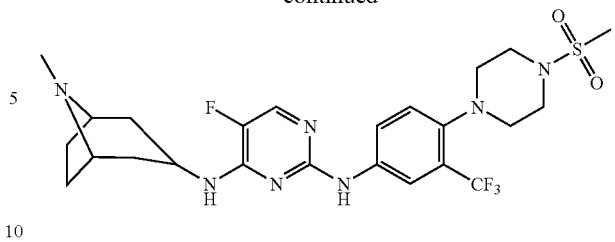

2-Chloro-5-fluoro-N4-(endo-8-methyl-8-azabicyclo[3.2.1]oct-3-yl)-4-pyrimidineamine HCl salt (80 mg) and [4-(4-methylsulfonylpiperazino)-3-trifluoromethyl]aniline (80 mg) were suspended in isopropanol (1 mL) and TFA (5 drops). The solution was heated at 100° C. overnight, then cooled to room temperature. The solution was evaporated and purified by HPLC to give 5-fluoro-N4-(endo-8-methyl-8-azabicyclo[3.2.1]oct-3-yl)-N2-[4-(4-methylsulfonylpiperazino)-3-trifluoromethyl]phenyl-2,4-pyrimidinediamine. $^1$H NMR (DMSO-d$_6$): δ 1.81-1.96 (m, 8H), 2.16 (m, 2H), 2.59 (s, 3H), 2.88 (br, 4H), 2.93 (s, 3H), 3.20 (br, 4H), 4.29 (m, 1H), 7.48 (m, 2H), 7.84 (s, 1H), 7.90 (d, J=4.2 Hz, 1H), 7.99 (d, J=8.4 Hz, 1H), 9.27 (s, 1H) ppm; $^{19}$F NMR (282 MHz, DMSO-d$_6$): δ-165.44, -59.87 ppm; LCMS: purity: 98.81%; MS (m/e): 558.11 (MH+).

Other examples included below can be prepared in a similar manner and using techniques well known in the art.

Example 2

Synthesis of N2-(3-chloro-4-methoxy)phenyl-5-fluoro-N4-(endo-8-methyl-8-azabicyclo[3.2.1]oct-3-yl)-2,4-pyrimidinediamine

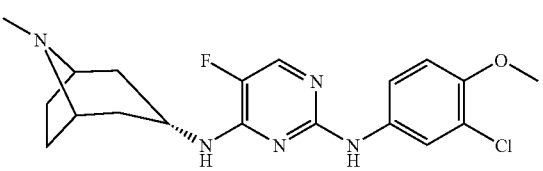

$^1$H NMR (DMSO-d$_6$): δ 1.85-2.00 (m, 6H), 2.10 (d, J=16.2 Hz, 2H), 2.26 (m, 2H), 2.66 (d, J=4.5 Hz, 3H), 3.79 (s, 3H), 4.26 (m, 1H), 7.02 (d, J=9.0 Hz, 1H), 7.42 (d, J=8.7 Hz, 1H), 7.59 (br, 1H), 7.77 (s, 1H), 7.90 (d, J=4.2 Hz, 1H), 9.08 (s, 1H), 9.39 (s, 1H) ppm; $^{19}$F NMR (282 MHz, DMSO-d$_6$): δ-165.93 ppm; LCMS: purity: 98.88%; MS (m/e): 392.13 (MH+).

Example 3

Synthesis of N2-(3-cyano)phenyl-5-fluoro-N4-(endo-8-methyl-8-azabicyclo[3.2.1]oct-3-yl)-2,4-pyrimidinediamine

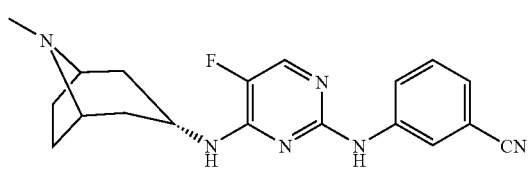

$^1$H NMR (DMSO-$d_6$): δ 1.89 (m, 6H), 2.15 (m, 2H), 2.55 (s, 3H), 4.31 (m, 1H), 7.30 (d, J=7.2 Hz, 1H), 7.41 (t, J=7.8 Hz, 1H), 7.50 (d, J=6.9 Hz, 1H), 7.87 (d, J=8.7 Hz, 1H), 7.93 (d, J=3.6 Hz, 1H), 8.15 (s, 1H), 9.43 (s, 1H) ppm; $^{19}$F NMR (282 MHz, DMSO-$d_6$): δ-164.94 ppm; LCMS: purity: 98.92%; MS (m/e): 353.24 (MH+).

Example 4

Synthesis of 5-fluoro-N4-(endo-8-methyl-8-azabicyclo[3.2.1]oct-3-yl)-N2-[4-(4-methylpiperazino)-3-trifluoromethyl]phenyl-2,4-pyrimidinediamine

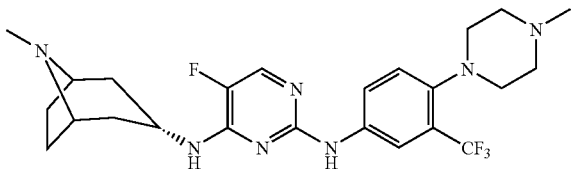

$^1$H NMR (DMSO-$d_6$): δ 1.89-1.99 (m, 6H), 2.10 (m, 2H), 2.26 (m, 2H), 2.67 (d, J=3.9 Hz, 3H), 2.87 (br, 4H), 3.01 (br, 4H), 3.04 (s, 3H), 4.25 (m, 1H), 7.43 (d, J=8.1 Hz, 1H), 7.59 (d, J=6.0 Hz, 1H), 7.95 (m, 3H), 9.29 (s, 1H), 9.41 (br, 1H), 9.68 (br, 1H) ppm; $^{19}$F NMR (282 MHz, DMSO-$d_6$): δ-170.77, -60.00 ppm; LCMS: purity: 93.19%; MS (m/e): 494.41 (MH+).

Example 5

Synthesis of N2-[3-chloro-4-(4-methylsulfonylpiperazino)]phenyl-5-fluoro-N4-(endo-8-methyl-8-azabicyclo[3.2.1]oct-3-yl)-2,4-pyrimidinediamine

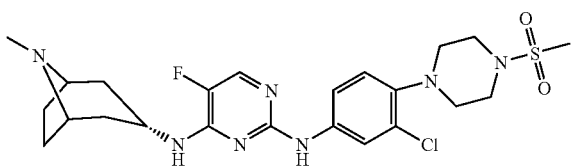

$^1$H NMR (DMSO-$d_6$): δ 1.81-1.92 (m, 8H), 2.15 (m, 2H), 2.56 (s, 3H), 2.93 (s, 3H), 2.97 (t, 4H), 3.25 (t, 4H), 4.28 (m, 1H), 7.08 (d, J=8.4 Hz, 1H), 7.41 (d, J=7.8 Hz, 1H), 7.50 (d, J=8.4 Hz, 1H), 7.82 (s, 1H), 7.88 (d, J=3.6 Hz, 1H), 9.10 (s, 1H) ppm; $^{19}$F NMR (282 MHz, DMSO-$d_6$): δ-166.04 ppm; LCMS: purity: 99.31%; MS (m/e): 524.05 (MH+).

Example 6

In Vitro IL-10 and IL-23 Assays

Abbreviations

THP-1: human acute monocyte leukemia cell line

IFNγ: interferon gamma

SAC: *Staphylococcus aureus* cells, heat-killed and formalin-fixed

IKK2VI inhibitor: (5-phenyl-2-ureido)thiophene-3-carbaxamide

A. Screening Protocol

Materials

THP-1 cells and RPMI growth media containing 1% P/S and 10% FBS

IFNγ (Peprotech, Cat No. 300-02)

White clear bottom 96 well plates (Fisher, Cat No. 07-200-587, Corning #3903)

SAC (12% solution from Calbiochem, Cat No. 507858)

CELL TITER GLO® reagent (Promega, Cat No. G7573)

Positive controls, IKK2VI inhibitor (Calbiochem, Cat No. 401483)

Exponentially growing THP-1 cells were plated (100K/well in 100 μL) in standard RPMI media (1% P/S+10% FBS) containing 50 ng/mL IFNγ (1000 U/mL) onto a white clear bottom 96 well plate and leave the cells in 37° C. incubator for 24 h.

After 24 h incubation, 100 μL of RPMI media containing 2× concentrated test compound per well was added to the above cell-culture media (compounds typically were assayed at a final concentration of from 0.01 μM to 20 μM). The plates were pre-incubated for 1 h at 37° C. before being stimulated with SAC.

After 1 h compound pre-incubation, 10 μL per well of 20× concentrated SAC solution in RPMI media was added to give a final concentration of 0.01%, the plates were shaken and incubated at 37° C. for an additional 18 h.

155 μL of the supernatant was harvested from each well and to the remaining 50 μL/well of the cell culture plate was added 50 μL of CELL TITER GLO® reagent. The plates were incubated for 1-2 minutes on a shaker and read for luminescence intensity to determine the compound cytotoxicity.

The cell culture supernatant collected above was used to carry out IL23 ELISA (65 μL-Supernatant) and IL10 ELISA (90 μL-Supernatant) as described below.

B. Human IL-23 (p19/p40) ELISA Protocol (e-Biosciences)

Materials 96-well high binding opaque white plates (from Pierce, Cat No. 15042)

1× PBS; 1× TBST washing buffer

Blocking Solution: 0.5% Casein in PBS (from BDH, Cat No. 440203H)

Dilution Solution: 1% BSA in PBS (10% BSA from Fisher, Cat No. 37525)

Capture antibody: Rat anti-human IL-23 (p19) (e-Biosciences, Cat. No. 14-7238-85)

Detection antibody: Primary Mouse Biotinylated anti-human IL-12 (p40/p70) (e-biosciences, Cat No. 13-7129-85); Secondary HRP-conjugated Streptavidin (R&D Systems, Cat No. DY998).

rHuman-IL-23 (e-biosciences, Cat No. 34-8239)

(Suggested starting concentration=5 ng/mL in RPMI cell culture media)

Cell Culture Supernatant (65 μL from THP-1 cells primed with IFN☐ (50 ng/mL-1000 U/mL) and stimulated with 0.01% SAC)

SUPERSIGNAL® ELISA Pico Chemiluminescent substrate [Pierce, Cat No. 37069]

Coating Plates:

To 10.5 mL PBS was added 50 μL of anti-IL23 (p19) capture antibody (2.5 μg/mL), mixed well and 100 μL of the coating solution was added to each well of the 96 well white plates from Pierce, cover and incubate overnight at 4° C.

Blocking the Plates:

The anti-IL23 (p19)-antibody-coated plates were washed 2× using TBST (use plate washer) and the plates were blocked using 200 μL of 0.5% Casein for 1.5-2 h at room temperature with shaking.

Addition of Supernatant and Detection:

The plates were washed 2× using TBST and the supernatant (65 μL/well) was transferred to the above pre-blocked/IL23 (p19)-antibody-coated 96 well plate and incubated at RT for 1.5 h with shaking.

The plate was washed 4× using TBST (plate washer) and 100 μL/well of detection antibody solution was added. The detection antibody solution was prepared from 2 μL of biotin labeled anti-IL-12 (p40/p70) antibody in 11 mL 1% BSA/PBS solution (1-5000 dilution). The plates were incubated for 1 hour with shaking at RT.

Again, the plate was washed 4× with TBST and 100 μL of HRP labeled Streptavidin (R&D Systems) solution (10 μL/10 mL 1% BSA solution) was added and incubated at RT for another 45 min with shaking.

After 45 min, the plate was washed with TBST 4× and 100 μL/well Super Signal ELISA Pico Chemiluminescent Substrate from Pierce (3.5 mL A+3.5 mL B+3.5 mL MQ water) was added, the plate was shaken for 1-2 minutes then read on a plate reader to quantify the amount of IL-23 secreted by the cells.

C. Human IL-10 ELISA Protocol (e-Biosciences)

Materials 96-well high binding opaque white plates (from Pierce, Cat No. 15042)

1× PBS; 1× TBST washing buffer

Blocking Solution: 0.5% Casein in PBS (from BDH, Cat No. 440203H)

Dilution Solution: 1% BSA in PBS (10% BSA from Fisher, Cat No. 37525)

Capture antibody: Rabbit anti-human IL-10 (e-Biosciences, Cat. No. 14-7108-85)

Detection antibody: Primary Mouse Biotinylated anti-human IL-10 (e-biosciences, Cat No. 13-7109-85); Secondary HRP-conjugated Streptavidin (R&D Systems, Cat No. DY998).

rHuman-IL-10 (e-biosciences, Cat No. 34-8109)

(Suggested starting concentration=1 ng/mL in RPMI cell culture media)

Cell Culture Supernatant (90 μL from THP-1 cells primed with IFNγ (50 ng/mL-1000 U/mL) and stimulated with 0.01% SAC)

SUPERSIGNAL® ELISA Pico Chemiluminescent substrate [Pierce, Cat No. 37069]

Coating Plates:

To 10.5 mL PBS was added 50 μL of anti-IL10 capture antibody (2.5 μg/mL), mixed well and 100 μL of the coating solution was added to each well of the 96 well white plates from Pierce. The plates were covered and incubated overnight at 4° C.

Blocking the Plates:

The anti-IL10 antibody-coated plates were washed 2× using TBST (use plate washer) and blocked the using 200 μL of 0.5% Casein for 1.5-2 h at RT with shaking.

Addition of Supernatant and Detection:

The plates were washed 2× using TBST and the supernatant (100 μL/well) was transferred to the above pre-blocked/IL10-antibody-coated 96 well plate and incubated at RT for 1.5 h with shaking.

The plate was washed 4× using TBST (plate washer) and 100 μL/well detection antibody solution prepared from 2 μL of biotin labeled anti-IL-10 antibody in 11 mL 1% BSA/PBS solution (1-5000 dilution) was added. The plates were incubated for 1 hour with shaking at RT.

Again, the plate was washed 4× with TBST and 100 μL of HRP labeled Streptavidin (R&D Systems) solution (10 μL/10 mL 1% BSA solution) was added and incubated at RT for another 45 min with shaking.

After 45 min, the plate was washed with TBST 4× and 100 μL/well Super Signal ELISA Pico Chemiluminescent Substrate from Pierce (3.5 mL A+3.5 mL B+3.5 mL MQ water) was added, the plate was shaken for 1-2 minutes then read on a plate reader to quantify the amount of IL-10 secreted by the cells.

D. Results

Data of compounds from this assay are reported in Table 1 below:

TABLE 1

| | STRUCTURE | IL-10 | IL-23 |
|---|---|---|---|
| 1 | 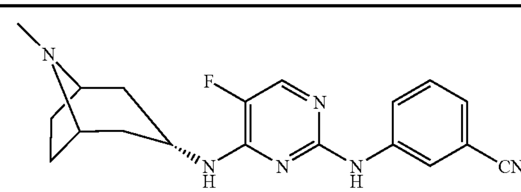 | + | − |
| 2 | 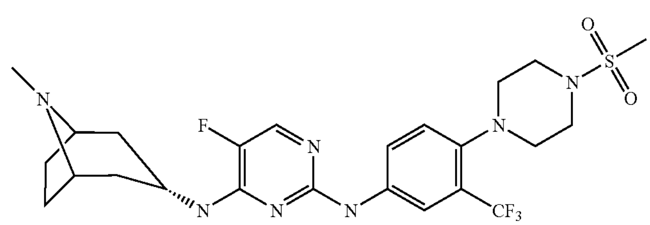 | + | − |
| 3 | 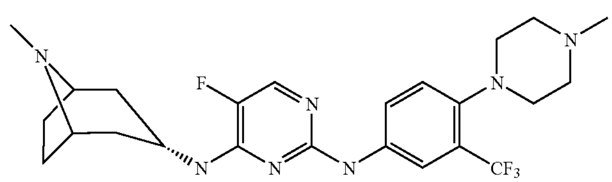 | − | − |

TABLE 1-continued

| | STRUCTURE | IL-10 | IL-23 |
|---|---|---|---|
| 4 | (structure) | + | − |

Table 1 shows the effect of the tested compounds on expression levels of IL-10 and IL-23 in THP-1 cells stimulated with SAC. "+" indicates an increase in production, and "−" indicates a decrease in production.

Example 7

Methods of Treatment

A. A compound described herein having anti-inflammatory activity is identified by a suitable method. A subject having an inflammatory disorder is identified by a suitable method. The subject is treated with the compound described herein by administering the compound in a carrier suitable for the chosen mode of administration in an amount effective for treating the inflammatory disorder.

B. A compound described herein having anti-inflammatory activity is identified by a suitable method. A subject having psoriasis is identified by a suitable method. The subject is treated with the compound described herein by administering the compound in a carrier suitable for the chosen mode of administration in an amount effective for treating the psoriasis.

C. A compound described herein having anti-inflammatory activity is identified by a suitable method. A subject having Crohn's disease is identified by a suitable method. The subject is treated with the compound described herein by administering the compound in a carrier suitable for the chosen mode of administration in an amount effective for treating the Crohn's disease.

D. A compound described herein having anti-inflammatory activity is identified by a suitable method. A subject having osteoarthritis is identified by a suitable method. The subject is treated with the compound described herein by administering the compound in a carrier suitable for the chosen mode of administration in an amount effective for treating the osteoarthritis.

E. A compound described herein that inhibits the production of IL-23 is identified by a suitable method. A subject having an inflammatory disorder is identified by a suitable method. The subject is treated with the compound described herein by administering the compound in a carrier suitable for the chosen mode of administration in an amount effective for treating the inflammatory disorder.

F. A compound described herein that increases the production of IL-10 is identified by a suitable method. A subject having an inflammatory disorder is identified by a suitable method. The subject is treated with the compound described herein by administering the compound in a carrier suitable for the chosen mode of administration in an amount effective for treating the inflammatory disorder.

G. A compound described herein that inhibits the production of IL-23 and increases the production of IL-10 is identified by a suitable method. A subject having an inflammatory disorder is identified by a suitable method. The subject is treated with the compound described herein by administering the compound in a carrier suitable for the chosen mode of administration in an amount effective for treating the inflammatory disorder.

H. A compound described herein that inhibits the production of IL-23 and inhibits the production of IL-10 is identified by a suitable method. A subject having an inflammatory disorder is identified by a suitable method. The subject is treated with the compound described herein by administering the compound in a carrier suitable for the chosen mode of administration in an amount effective for treating the inflammatory disorder.

I. A compound described herein that increases the production of IL-10 and increases the production of IL-23 is identified by a suitable method. A subject having an inflammatory disorder is identified by a suitable method. The subject is treated with the compound described herein by administering the compound in a carrier suitable for the chosen mode of administration in an amount effective for treating the inflammatory disorder.

While the invention has been described with reference to specific embodiments, variations and modifications may be made without departing from the spirit and the scope of the invention. Such variations and modifications are to be considered within the purview and scope of the invention as defined by the appended claims.

All of the above-mentioned references are herein incorporated by reference in their entirety to the same extent as if each individual reference was specifically and individually indicated to be incorporated herein by reference in its entirety.

We claim:

1. A compound according to the formula:

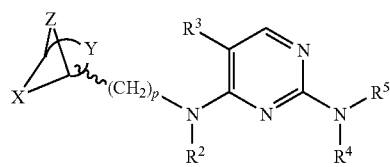

wherein:

X represents $(CH_2)_m$ wherein m is an integer from 1 to 4, and one or more $CH_2$ are optionally replaced with O, S or $N(R^{O1})$ wherein $R^{O1}$ represents H, $C_1$-$C_7$ alkyl or $C_3$-$C_8$ cycloalkyl;

Y represents $(CH_2)_n$ wherein n is an integer from 2 to 5, and one or more $CH_2$ are optionally replaced with O, S or $N(R^{O2})$ wherein $R^{O2}$ represents H, $C_1$-$C_7$ alkyl or $C_3$-$C_8$ cycloalkyl;

Z represents N(R¹), O or S, wherein R¹ represents H, $C_1$-$C_7$ alkyl or $C_3$-$C_8$ cycloalkyl;

〰〰 represents a bond having an endo-configuration, an exo-configuration, or a mixture thereof;

p is 0 or 1;

R² represents H, $C_1$-$C_7$ alkyl or $C_2$-$C_8$ alkanoyl;

R³ represents F;

R⁴ represents H, $C_1$-$C_7$ alkyl or $C_2$-$C_8$ alkanoyl; and

R⁵ represents a substituted aryl or heteroaryl.

2. The compound of claim 1, represented by the formula:

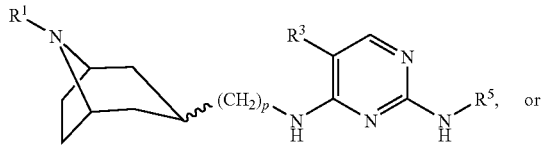

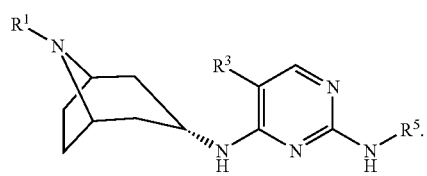

3. The compound of claim 1, wherein R⁵ represents substituted aryl or heteroaryl having 6 ring atoms.

4. The compound of claim 3, wherein R⁵ represents one of the following formulae:

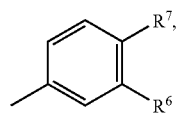 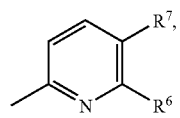

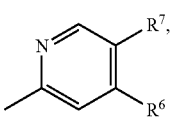 and 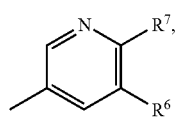

wherein R⁶ represents halogen, cyano, $C_1$-$C_7$ alkyl, $C_1$-$C_7$ haloalkyl, $C_1$-$C_7$ alkoxy or $C_1$-$C_7$ haloalkoxy; and R⁷ represents H, $C_1$-$C_7$ alkyl, $C_1$-$C_7$ haloalkyl, $C_1$-$C_7$ alkoxy, $C_1$-$C_7$ haloalkoxy, $C_3$-$C_8$ cycloalkyl, —$SO_2$—$C_3$-$C_8$ cycloalkyl, $C_3$-$C_8$ cycloalkyl-$SO_2$—R⁸, $C_3$-$C_8$ cycloalkyl, —$SO_2$—$C_3$-$C_8$ cycloalkenyl, $C_3$-$C_8$ cycloalkenyl-$SO_2$—R⁸, aryl, —$SO_2$-aryl, aryl-$SO_2$—R⁸, a heterocyclic group, a —$SO_2$-heterocyclic group, a heterocyclic-$SO_2$—R⁸ group, or —$SO_2$—NR⁹R¹⁰, wherein R⁸ and R⁹ each independently represents $C_1$-$C_7$ alkyl or $C_3$-$C_8$ cycloalkyl, and R¹⁰ represents H, $C_1$-$C_7$ alkyl or $C_3$-$C_8$ cycloalkyl; or R⁶ and R⁷ are combined to form a ring together with the carbon atoms to which they are bonded, provided that when R⁶ is halogen, X is (CH₂)₂, Y is (CH₂)₃ and Z is N(R¹), one or more of R¹ to R⁴ and R⁷ is not H.

5. The compound of claim 4, wherein the heterocyclic group encompassed by R⁷: (a) is aromatic, aliphatic or unsaturated, spiro, fused or bridged; (b) has 3 to 14 carbon ring atoms, at least one of which is replaced with O, S or N(R⁰³) wherein R⁰³ represents H, $C_1$-$C_7$ alkyl or $C_3$-$C_8$ cycloalkyl;

(c) has 1 to 3 rings; and/or (d) is selected from the group consisting of aziridinyl, oxiranyl, thiiranyl, azetidinyl, oxetanyl, thietanyl, pyrrolidinyl, tetrahydrofuryl, tetrahydrothienyl, piperidyl, tetrahydropyranyl, tetrahydrothiopyranyl, tetrahydropyridyl, tetrahydroquinolyl, tetrahydroisoquinolyl, morpholinyl, thiomorpholinyl, piperazinyl, dioxolanyl, imidazolidinyl, oxazolidinyl, isoxazolidinyl, thiazolidinyl, pyrazolidinyl, 2H-pyrrolyl, pyrrolinyl, imidazolinyl, pyrazolinyl, dihydrofuryl, dihydrothienyl, dihydropyranyl, dihydrothiopyranyl, dihydropyridyl, dihydroquinolyl, dihydroisoquinolyl, indolinyl, isoindolinyl, furyl, furazanyl, pyranyl, thienyl, pyrrolyl, pyrazolyl, imidazolyl, triazolyl, tetrazolyl, oxazolyl, oxadiazolyl, isoxazolyl, thiazolyl, isothiazolyl, pyridyl, pyridazinyl, pyrimidinyl, pyrazinyl, triazinyl, benzopyranyl, benzofuranyl, indolyl, and quinolinyl.

6. The compound of claim 4, represented by the formula:

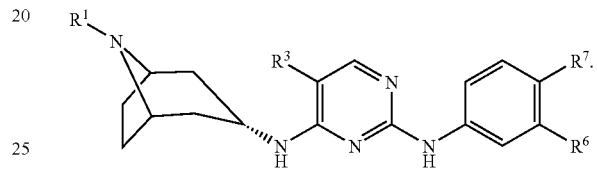

7. The compound of claim 6, wherein R⁶ represents halogen or $C_1$-$C_7$ haloalkyl.

8. The compound of claim 7, wherein R⁶ represents Cl or $CF_3$.

9. The compound of claim 4, represented by the formula:

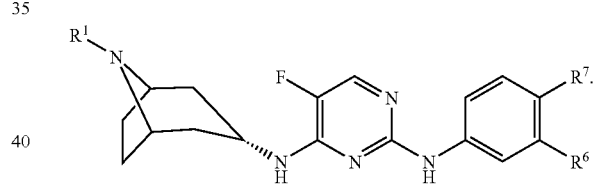

10. The compound of claim 9, wherein R⁶ represents $CF_3$.

11. The compound of claim 10, wherein R⁷ represents the following formula:

H, $C_1$-$C_7$ alkoxy,

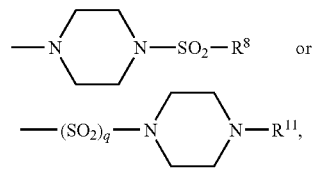

wherein q represents 0 or 1, and R¹¹ represents H or $C_1$-$C_7$ alkyl.

12. The compound of claim 11, wherein R⁸ represents methyl or cyclopropyl.

13. The compound of claim 1, wherein: (a) R³ represents F; (b) R² and/or R⁴ represent H; and/or (c) X represents (CH₂)₂, Y represents (CH₂)₃, and Z represents N(R¹).

14. The compound of claim 13, wherein R¹ represents $CH_3$.

15. The compound of claim 1, represented by one of the following formulae:

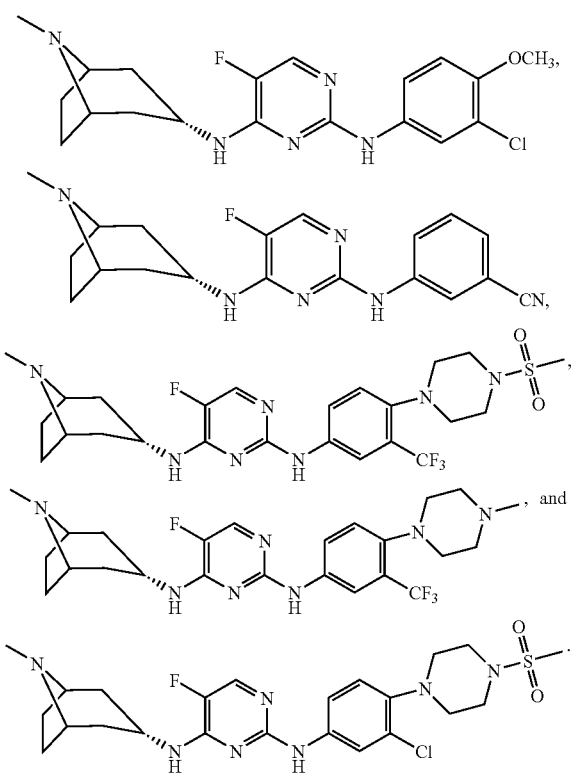

16. A composition comprising one or more compounds of claim 1.

17. A method for preparing the compound of claim 1, comprising:
(a) reacting a substituted or unsubstituted uracil with a halogenating agent, to obtain a 2,4-dichloropyrimidine compound;
(b) reacting the 2,4-dichloropyrimidine compound with

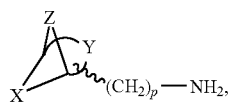

to obtain a 4N- substituted-4-pyrimidineamine derivative;
(c) reacting the 4N-substituted-4-pyrimidineamine derivative with $R^5NH_2$, to obtain a 2,4-pyrimidinediamine derivative; and
(d) reacting the 2,4-pyrimidinediamine derivative with $R^2$-LG, wherein $R^2$ is not H and LG represents a leaving group, to thereby obtain the compound of claim 1, wherein $R^4$ is H.

18. A method for preparing the compound of claim 1, comprising:
(a) converting a substituted or unsubstituted cytosine into a N4-protected cytosine;
(b) reacting the N4-protected cytosine with a halogenating agent, to obtain a 2-chloro-4N-protected-4-pyrimidine amine;
(c) reacting the 2-chloro-4N-protected-4-pyrimidine amine with $R^5NH_2$, to obtain a 4N-protected -2,4-pyrimidinediamine derivative;

(d) deprotecting the 4N-protected-2,4-pyrimidinediamine derivative, to obtain a 2,4-pyrimidinediamine derivative; and
(e) reacting the 2,4-pyrimidinediamine derivative with

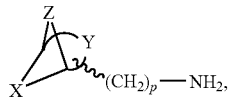

to obtain the compound of claim 1, wherein $R^2$ and $R^4$ are H.

19. A method for preparing the compound of claim 1, comprising:
(a) reacting a substituted or unsubstituted cytosine with unprotected

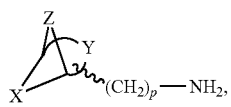

to obtain a N4-substituted cytosine derivative;
(b) reacting the N4-substituted cytosine derivative with a halogenating agent, to obtain a 2-chloro-N4-substituted-pyrimidineamine derivative; and
(c) reacting the 2-chloro-N4-substituted-pyrimidineamine derivative with $R^5NH_2$, to thereby obtain the compound of claim 1, wherein $R^2$ and $R^4$ are H.

20. A method for preparing the compound of claim 1, comprising:
(a) reacting a substituted or unsubstituted cytosine with protected

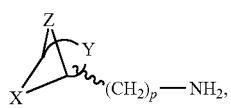

to obtain a protected N4-substituted cytosine derivative;
(b) reacting the protected N4-substituted cytosine derivative with a halogenating agent, to obtain a protected 2-chloro-N4-substituted-pyrimidineamine derivative;
(c) reacting the protected 2-chloro-N4-substituted-pyrimidineamine derivative with $R^5NH_2$, to obtain a protected 2,4-pyrimidinediamine compound; and
(d) deprotecting the protected 2,4-pyrimidinediamine compound to thereby obtain the compound of claim 1, wherein $R^2$ and $R^4$ are H.

21. A method for preparing the compound of claim 1, comprising:
(a) reacting a substituted 2-amino-4-pyrimidinol with $R^5$-LG, wherein LG represents a leaving group, to obtain a N2-substituted-4-pyrimidinol;
(b) reacting the N2-substituted-4-pyrimidinol with a halogenating agent, to obtain a N2-substituted 4-halo-2-pyrimidine amine; and (c) reacting the N2-substituted 4-halo-2-pyrimidine amine with

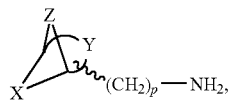

to obtain the compound of claim 1, wherein $R^2$ and $R^4$ are H.

22. A method for inhibiting production of IL-23, comprising administering to a subject in need thereof a therapeutically effective amount of one or more compounds according to the formula:

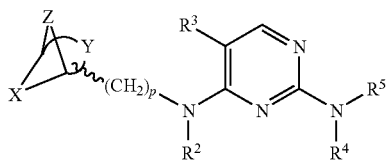

wherein:
X represents $(CH_2)_m$ wherein m is an integer from 1 to 4, and one or more $CH_2$ are optionally replaced with O, S or $N(R^{01})$ wherein $R^{01}$ represents H, $C_1$-$C_7$ alkyl or $C_3$-$C_8$ cycloalkyl;
Y represents $(CH_2)_n$ wherein n is an integer from 2 to 5, and one or more $CH_2$ are optionally replaced with O, S or $N(R^{02})$ wherein $R^{02}$ represents H, $C_1$-$C_7$ alkyl or $C_3$-$C_8$ cycloalkyl;
Z, represents $N(R^1)$, O or S, wherein $R^1$ represents H, $C_1$-$C_7$ alkyl or $C_3$-$C_8$ cycloalkyl;
∼∼∼ represents a bond having an endo-configuration, an exo-configuration, or a mixture thereof;
p is 0 or 1;
$R^2$ represents H, $C_1$-$C_7$ alkyl or $C_2$-$C_8$ alkanoyl;
$R^3$ represents F;
$R^4$ represents H, $C_1$-$C_7$ alkyl or $C_2$-$C_8$ alkanoyl; and
$R^5$ represents a substituted aryl or heteroaryl.

23. The method of claim 22, wherein: (a) the method further comprises stimulating production of IL-10; and/or (b) the subject is a human.

24. A method for stimulating production of IL-10, comprising administering to a subject in need thereof a therapeutically effective amount of one or more compounds according to the formula:

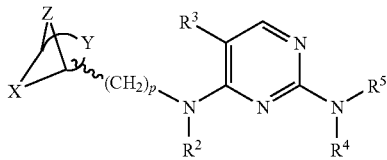

wherein:
X represents $(CH_2)_m$ wherein m is an integer from 1 to 4, and one or more $CH_2$ are optionally replaced with O, S or $N(R^{01})$ wherein $R^{01}$ represents H, $C_1$-$C_7$ alkyl or $C_3$-$C_8$ cycloalkyl;
Y represents $(CH_2)_n$ wherein n is an integer from 2 to 5, and one or more $CH_2$ are optionally replaced with O, S or $N(R^{02})$ wherein $R^{02}$ represents H, $C_1$-$C_7$ alkyl or $C_3$-$C_8$ cycloalkyl;

Z represents $N(R^1)$, O or S, wherein $R^1$ represents H, $C_1$-$C_7$ alkyl or $C_3$-$C_8$ cycloalkyl;
∼∼∼ represents a bond having an endo-configuration, an exo-configuration, or a mixture thereof;
p is 0 or 1;
$R^2$ represents H, $C_1$-$C_7$ alkyl or $C_2$-$C_8$ alkanoyl;
$R^3$ represents F;
$R^4$ represents H, $C_1$-$C_7$ alkyl or $C_2$-$C_8$ alkanoyl; and
$R^5$ represents a substituted aryl or heteroaryl.

25. A compound of formula (VI):

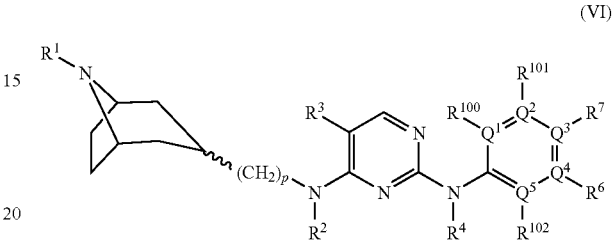

wherein
$R^1$ represents H, $C_1$-$C_7$ alkyl or $C_3$-$C_8$ cycloalkyl;
$R^2$ represents H, $C_1$-$C_7$ alkyl or $C_2$-$C_8$ alkanoyl;
$R^3$ represents F;
$R^4$ represents H, $C_1$-$C_7$ alkyl or $C_2$-$C_8$ alkanoyl;
p is 0 or 1;
$Q^1$, $Q^2$, $Q^3$, $Q^4$, and $Q^5$ are independently selected from C and N;
$R^6$, $R^7$, $R^{100}$, $R^{101}$, and $R^{102}$ are independently selected from H, halogen, cyano, $C_1$-$C_7$ alkyl, $C_1$-$C_7$ haloalkyl, $C_1$-$C_7$ alkoxy, $C_1$-$C_7$ haloalkoxy, $C_3$-$C_8$ cycloalkyl, —$SO_2$—$C_3$-$C_8$ cycloalkyl, $C_3$-$C_8$ cycloalkyl-$SO_2$—$R^8$, $C_3$-$C_8$ cycloalkyl, —$SO_2$—$C_3$-$C_8$ cycloalkenyl, $C_3$-$C_8$ cycloalkenyl-$SO_2$—$R^8$, aryl, —$SO_2$-aryl, aryl-$SO_2$—$R^8$, a heterocyclic group, a —$SO_2$-heterocyclic group, a heterocyclic-$SO_2$—$R^8$ group, or —$SO_2$—$NR^9R^{10}$; or
any two of $R^6$, $R^7$, $R^{100}$, $R^{101}$, and $R^{102}$ that are vicinal are combined to form a ring together with the carbon atoms to which they are bonded; and
any of $R^6$, $R^7$, $R^{100}$, $R^{101}$, and $R^{102}$ is absent to satisfy valence requirements;
wherein $R^8$ and $R^9$ each independently represents $C_1$-$C_7$ alkyl or $C_3$-$C_8$ cycloalkyl, and $R^{10}$ represents H, $C_1$-$C_7$ alkyl or $C_3$-$C_8$ cycloalkyl.

26. A compound of formula (VII):

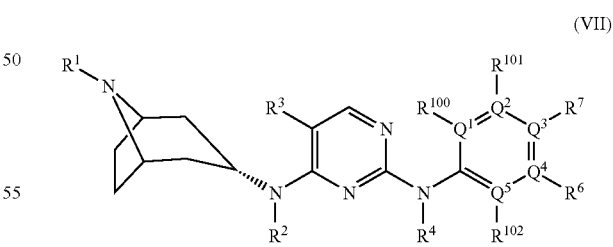

wherein $R^1$ represents H, $C_1$-$C_7$ alkyl or $C_3$-$C_8$ cycloalkyl;
$R^2$ represents H, $C_1$-$C_7$ alkyl or $C_2$-$C_8$ alkanoyl;
$R^3$ represents F;
$R^4$ represents H, $C_1$-$C_7$ alkyl or $C_2$-$C_8$ alkanoyl;
$Q^1$, $Q^2$, $Q^3$, $Q^4$, and $Q^5$ are independently selected from C and N;
$R^6$, $R^7$, $R^{100}$, $R^{101}$, and $R^{102}$ are independently selected from H, halogen, cyano, $C_1$-$C_7$ alkyl, $C_1$-$C_7$ haloalkyl, $C_1$-$C_7$ alkoxy, $C_1$-$C_7$ haloalkoxy, $C_3$-$C_8$ cycloalkyl, —$SO_2$—$C_3$-$C_8$ cycloalkyl, $C_3$-$C_8$ cycloalkyl-$SO_2$—$R^8$, $C_3$-$C_8$ cycloalkyl, —$SO_2$—$C_3$-$C_8$ cycloalkenyl, $C_3$-$C_8$ cycloalkenyl-$SO_2$—$R^8$, aryl, —$SO_2$-aryl, aryl-$SO_2$—$R^8$, a heterocyclic group, a —$SO_2$-heterocyclic group, a heterocyclic-$SO_2$—$R^8$ group, or —$SO_2$—$NR^9R^{10}$; or any two of $R^6$, $R^7$, $R^{100}$, $R^{101}$, and $R^{102}$ that are vicinal are combined to form a ring together with the carbon atoms to which they are bonded; and any of $R^6$, $R^7$, $R^{100}$, $R^{101}$, and $R^{102}$ is absent to satisfy valence requirements;

wherein $R^8$ and $R^9$ each independently represents $C_1$-$C_7$ alkyl or $C_3$-$C_8$ cycloalkyl, and $R^{10}$ represents H, $C_1$-$C_7$ alkyl or $C_3$-$C_8$ cycloalkyl.

* * * * *